US006274065B1

(12) United States Patent
Deno et al.

(10) Patent No.: US 6,274,065 B1
(45) Date of Patent: *Aug. 14, 2001

(54) PROCESS FOR THE PREPARATION OF FLUORESCENT COMPOSITIONS, FLUORESCENT COMPOSITIONS AND THEIR USE

(75) Inventors: Takashi Deno, Nishinomiya; Kunihiko Kodama, Takarazuka, both of (JP); Abul Iqbal, Arconciel (CH); Brian Gerrard Devlin, Takarazuka (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/017,871

(22) Filed: Feb. 3, 1998

(30) Foreign Application Priority Data

| Feb. 3, 1997 | (EP) | ................................................ | 97810049 |
| Feb. 3, 1997 | (EP) | ................................................ | 97810050 |
| Feb. 3, 1997 | (EP) | ................................................ | 97810051 |
| Feb. 4, 1997 | (EP) | ................................................ | 97810054 |
| Feb. 4, 1997 | (EP) | ................................................ | 97810055 |

(51) Int. Cl.$^7$ .................................................. C09K 11/06
(52) U.S. Cl. .................... 252/301.16; 106/494; 106/495; 106/496; 106/497; 106/498; 252/301.21; 252/301.22; 252/301.23; 252/301.24; 252/301.15; 252/301.26; 252/301.27; 252/301.28; 252/301.29; 252/301.31; 252/301.32; 252/301.34; 252/301.35
(58) Field of Search .................... 106/494, 495, 106/496, 497, 498; 252/301.16, 301.21, 301.22, 301.23, 301.24, 301.25, 301.26, 301.27, 301.28, 301.29, 301.31, 301.32, 301.34, 301.35

(56) References Cited

U.S. PATENT DOCUMENTS

| 4,452,720 | * | 6/1984 | Harada et al. | ................... | 252/301.16 |
| 4,627,997 | * | 12/1986 | Ide | ....................... | 428/690 |
| 5,084,205 | * | 1/1992 | Auslander | ....................... | 252/301.16 |
| 5,227,252 | * | 7/1993 | Murayama et al. | ................. | 428/690 |
| 5,296,331 |   | 3/1994 | Taguchi | ................................. | 430/253 |
| 5,565,328 | * | 10/1996 | Bascomb et al. | ...................... | 435/25 |
| 5,942,189 | * | 8/1999 | Wolfbeis et al. | .................. | 422/82.08 |

FOREIGN PATENT DOCUMENTS

| 456609 | * | 11/1991 | (EP) . |
| 0456609 |   | 11/1991 | (EP) . |
| 654711 | * | 5/1995 | (EP) . |
| 2292947 |   | 3/1996 | (GB) . |
| 5-320633 | * | 12/1993 | (JP) . |
| 9323492 |   | 11/1993 | (WO) . |
| 93/23492 | * | 11/1993 | (WO) . |
| 9415441 |   | 7/1994 | (WO) . |

OTHER PUBLICATIONS

Derwent Abst. 94–018671 [03], For JP 5–320633, May 25, 1992.

Tang et al, "Electroluminescence of Doped Organic Thin Films", J. Appl. Phys. Vol. 665 (9), pp. 3610–16, May 1, 1989.*

Port et al, "Host–Guest Energy Transfer Via Dipole–Dipole Interaction in Doped Fluorene Crsytals"Z Naturforsch. 36a, pp. 697–704, 1981 no month.*

Lang et al, "High–Pressure Study of Energy Transfer Between Coumarin 138 and Rhodamine B in a Solid Polymeric Matrix", J. Phy. Chem., vol. 97, No. 19, pp. 5058–5064. 1993 no month.*

* cited by examiner

*Primary Examiner*—C. Melissa Koslow
(74) *Attorney, Agent, or Firm*—David R. Crichton

(57) ABSTRACT

Preparation of a solid fluorescent composition comprising (1) mixing a host chromophore and an effective amount of a pigment precursor in a solvent, then generating a pigment as guest chromophore in-situ from the pigment precursor, and, subsequently, isolating the mixture of the host and guest chromophores, thereby forming a solid solution, or (2) mixing a polymer as a matrix or a polymer precursor and a pigment precursor in a solvent, if desired in the presence of a chromophore being a host component, then generating a pigment in-situ from the pigment precursor (being the guest component if a host component is present), and, subsequently, isolating the mixture of polymer and pigment, and—if present—the host component, thereby forming a solid solution, wherein in all cases where there is a host component, the absorption spectrum of the pigment (guest chromophore) overlaps with the fluorescence emission spectrum of the host chromophore.

4 Claims, No Drawings

PROCESS FOR THE PREPARATION OF FLUORESCENT COMPOSITIONS, FLUORESCENT COMPOSITIONS AND THEIR USE

The invention relates to a process for the preparation of a solid fluorescent composition comprising (1) mixing a host chromophore and an effective amount of a pigment precursor in a solvent, then generating a pigment as guest chromophore in-situ from the pigment precursor, and, subsequently, isolating the mixture of the host and guest chromophores, thereby forming a solid solution, or (2) mixing a polymer as a matrix or a polymer precursor and a pigment precursor in a solvent, if desired in the presence of a chromophore being a host component, then generating a pigment in-situ from the pigment precursor (being the guest component if a host component is present), and, subsequently, isolating the mixture of polymer and pigment, and—if present—the host component, thereby forming a solid solution, wherein in all cases where there is a host component, the absorption spectrum of the pigment (guest chromophore) overlaps with the fluorescence emission spectrum of the host chromophore.

In addition, the present invention relates to a composition comprising a polymer matrix or a polymer precursor, and/or a host chromophore, and a pigment precursor or a pigment, wherein in all cases where there is a host component, the absorption spectrum of the pigment (as guest chromophore), obtainable from the pigment precursor, overlaps with the fluorescence emission spectrum of the host chromophore, a process for the preparation of a powder, a powder, a process for the preparation of a layer on a solid support material and the use of the abovementioned compositions and the powder as fluorescent materials.

Combinations consisting of host chromophores and guest chromophores dissolved in the host matrix to generate an enhanced fluorescence and a Stoke shift of the emission fluorescence through an energy transfer from the host to the guest are highly desired materials in many technical applications.

The possibility of energy transfer between chromophores that possess overlapping emission and excitation wavelengths of host and guest chromophores is known. For example, H. Port et al. describe in Z. Naturforsch., 36a, pages 697 to 704 (1981) mixed crystals of fluorene doped with dibenzofurane (or benzindan) which possess an enhanced fluorescence in the UV region, at temperatures below 100K. Although low temperature fluorescence has no practical value and is only of scientific interest.

C. W. Tang et al. disclose in J. Appl. Phys., 65, 3610 to 3616 (1989) a multilayer electroluminescent device with a light emitting layer composed of 8-hydroxyquinoline aluminum, in which is embedded a zone doped with a fluorescent molecule e.g. coumarin. The device shows improved electroluminescence and a large gap between the excitation and emission wavelengths. This Stoke's shift is dependent on the dopant employed. The manufacture of the device is complicated and not suitable for an industrial production.

J. M. Lang et al. describe in J. Phys. Chem. 97, pages 5058 to 5064 (1993) the combination of coumarin as host and rhodamine as guest whereby both components are dissolved in polyacrylic acid, but enhanced fluorescence is possible only under high pressure.

In WO 93/23492 are disclosed fluorescent microparticles with an enhanced Stokes shift, which are composed of soluble and fluorescent host and guest dyes absorbed or bonded to polymeric microparticles. The material is used for the optical detection of nucleic acids like DNA or RNA. Unfavorably, the solid state fluorescence of these microparticles is poor.

U.S. Pat. No. 5,227,252 discloses a fluorescent composition comprising a support material which is coated on one side with a layer of 8-hydroxyquinoline aluminum, as host, and a derivative of quinacridone, as guest. Similarly, JP-A-05 320 633 discloses a fluorescent composition comprising a support material which is coated on one side with a layer of 8-hydroxyquinoline aluminum, as host, and a diketopyrrolopyrrole, as guest. Although the guest structures are inherently insoluble materials, they are in fact dissolved mainly as microsized clusters, which is a consequence of the applied co-sublimation manufacturing process. The materials possess an enhanced Stoke shift fluorescence and are used for example as light emitting materials in electroluminescent devices. The sublimation temperatures of the used chromophores are quite different. The process for their manufacture, which is a co-sublimation of both components, placed in different containers, requires large expenditures of technical equipment for precise control of the different sublimation conditions like temperature to achieve uniform layers on the support. The process is not suitable for large scale industrial manufacture. The process is also not suitable for the production of powders, which are highly desired materials.

In EP-A-0 456 609 is disclosed a process for the preparation of 1,2,3,4-tetrachloro-benzo[4,5]imidazo[2,1-a]isoindol-11-one and its derivatives in the presence of selected solvents. They are pigments which display solid state fluorescence and improved outdoor durability. It is also mentioned therein, that the combination of 95% 1,2,3,4-tetrachloro-benzo[4,5]imidazo[2,1-a]isoindol-11-one with 5% of Indanthrone Blue generates a green fluorescent pigment. Such a system is a pigment composite, wherein the new color generated is simply a sum of the two component colors. The color is not created by virtue of the occurrence of complex, molecular level, energy transfer processes that require close interaction between the components of the mixture.

EP 0 654 711 A discloses a means for preparing structured color images via the use of a soluble pigment precursor, which can be subsequently transformed, by the use of chemical, thermal, photolytic or radiative means, to generate an insoluble, nanosize, stable pigment thereof. The composition is specific to the generation of aggregated pigment particles that are dispersed homogeneously throughout a polymer matrix. Thus the compositions show the color of the pigment and are not fluorescent.

Hence, the object of the invention on hand was to provide a fluorescent composition, which does not show the abovementioned disadvantages, preferably a composition should be provided whereby a highly uniform distribution of inherently insoluble pigment in a matrix of a host chromophore or in a polymer matrix is achieved;

a solid solution is achieved, wherein an insoluble pigment is dissolved, preferably in a molecularly state, and thus is distributed, preferably homogeneously, in a matrix of a host chromophore;

fluorescent materials are generated from polymers as matrix and contain a dissolved pigment;

fluorescent materials with enhanced luminescence are obtained by the co-use of a host chromophore and energy transfer from the host to the pigment even in a polymer matrix;

the manufacturing process is far less expensive than known processes, particularly compared with the known co-sublimation technique;

the space-time-yield is improved;

an economic industrial scale production is achieved;

even an easy preparation of fluorescent particles comprising a host chromophore matrix and a pigment is achieved;

fluorescent layers of a host chromophore matrix and a pigment directly are obtained from a powder from host chromophore/pigment mixtures;

fluorescent layers of a host chromophore matrix and a pigment directly are obtained from a powder from host chromophore/pigment precursor mixtures;

Further, enhancement factors for the present invention preferably should be all positive and should be at least 1.3, preferably at least 2 and more preferably at least 5. The term "enhancement factor" as used herein, is defined as the increased or decreased factor, in terms of peak height emission intensities of a solid-state composition comprising of host and guest fluorescent moieties compared to an identical polymer that does not contain fluorescent guest moieties. Comparisons are considered real, for as long as the excitation radiation wavelengths are identical. Naturally however the emission wavelengths of host/guest material occurs at longer wavelengths (lower energy) as compared to an identical material with no guest component.

Accordingly, a process for the preparation of a solid fluorescent composition was found comprising (1) mixing a host chromophore and an effective amount of a pigment precursor in a solvent, then generating a pigment as guest chromophore in-situ from the pigment precursor, and, subsequently, isolating the mixture of the host and guest chromophores, thereby forming a solid solution, or (2) mixing a polymer as a matrix or a polymer precursor and a pigment precursor in a solvent, if desired in the presence of a chromophore being a host component, then generating a pigment in-situ from the pigment precursor (being the guest component if a host component is present), and, subsequently, isolating the mixture of polymer and pigment, and—if present—the host component, thereby forming a solid solution, wherein in all cases where there is a host component, the absorption spectrum of the pigment (guest chromophore) overlaps with the fluorescence emission spectrum of the host chromophore.

In addition, a composition comprising a polymer matrix or a polymer precursor, and/or a host chromophore, and a pigment precursor or a pigment, wherein in all cases where there is a host component, the absorption spectrum of the pigment (as guest chromophore), obtainable from the pigment precursor, overlaps with the fluorescence emission spectrum of the host chromophore, a process for the preparation of a powder, a powder, a process for the preparation of a layer on a solid support material and the use of the abovementioned compositions and the powder as fluorescent material were found, too.

A first embodiment of the invention on hand is a process for the preparation of a solid fluorescent composition comprising (1) mixing a host chromophore and an effective amount of a pigment precursor in a solvent, then generating a pigment as guest chromophore in-situ from the pigment precursor, and, subsequently, isolating the mixture of the host and guest chromophores, thereby forming a solid solution, or (2) mixing a polymer as a matrix or a polymer precursor and a pigment precursor in a solvent, if desired in the presence of a chromophore being a host component, then generating a pigment in-situ from the pigment precursor (being the guest component if a host component is present), and, subsequently, isolating the mixture of polymer and pigment, and—if present—the host component, thereby forming a solid solution, wherein in all cases where there is a host component, the absorption spectrum of the pigment (guest chromophore) overlaps with the fluorescence emission spectrum of the host chromophore.

In the context of this invention, the meaning of the overlap of the absorption spectrum of the guest chromophore with the fluorescence emission spectrum of the host chromophore, is clear to a skilled person in this field. However, to facilitate the understanding to others, overlap means "spectral overlap" defined by the following integral $$S = \int_0^{+\infty} f_F(v) f_A(v) dv$$

wherein $f_F(v)$ is normalized, so that $\int_0^{+\infty} f_F(v) \, dv$ is equal to fluorescence quantum yield of the host, and where $v$ is the wave number, $f_F$ the fluorescence spectrum of the host measured in quanta, and $f_A$ the spectral distribution of the molar extinction coefficient of the guest. The spectral overlap to realize photoluminescence enhancement usually is greater than 10, preferably greater than 100, more preferably greater than 500. An upper limit makes no sense, because the quantity "overlap" has no maximum (i.e. the larger, the better)).

In a preferred embodiment of the above process the in-situ generation of the pigment is carried out under conditions that avoid migration of the deliberated pigment. Usually this can be done by choosing a reaction temperature below 250° C., preferably in the range of from 10 to 250° C.

In another preferred embodiment of the above processes the in-situ generated pigment is distributed homogeneously within the mixture of host chromophore and pigment or within the polymer matrix.

In the context of this invention, the term "homogeneously" means that the molecules of the in-situ generated pigment are evenly or uniformly distributed or dispersed throughout the mixture or the polymer matrix, and, preferably in the ideal case are essentially equidistant from each other. According to observations today, the more even or uniform the distribution is, the better are the fluorescence properties. Furthermore, a homogeneous or even distribution is preferred, because usually the chances for aggregation are decreased.

Another preferred embodiment of the present invention relates to a process for the preparation of a solid fluorescent composition comprising (1) a host chromophore and distributed therein, preferably dissolved and homogeneously distributed therein, a pigment, wherein the amount of pigment preferably is at most 10 weight percent of the total composition or (2) a polymer matrix or polymer precursor and distributed therein, preferably dissolved and homogeneously distributed therein, a pigment, wherein the amount of pigment preferably is at most 10 weight percent of the total composition, alone or together with a host chromophore, in all cases where there is a host component, the absorption spectrum of the pigment overlaps with the fluorescence emission spectrum of the host chromophore, wherein preparation of both (1) and (2) employ pigment precursors, and to form the composition the ingredients are dissolved in a solvent, optionally polymerized, and subsequently isolated to form a solid solution, wherein the pigment is then generated in-situ from the pigment precursor in decomposing said pigment precursor under heating conditions, which avoid migration of the deliberated pigment.

Under the aspects of the invention solubility of host chromophores means that at least 10 mg, more preferably at least 50 mg and most preferably at least 100 mg of the host chromophores are soluble in 1 liter of solvent like dimethylformamide, at 20° C. It is self-evident, that the solubilities are higher at increased temperatures and depend on the solvent choice.

Under the aspects of the invention solubility of pigment precursors means that at least 200 mg, more preferably at least 300 mg and most preferably at least 500 mg of the pigment precursors are soluble in 1 liter of solvent like dimethylformamide at 20° C. It is self-evident, that the solubilities are higher at increased temperatures and depend on the solvent choice.

Under the aspects of the invention insolubility of pigments means that less than 500 mg, preferably less than 300 mg, more preferably less than 200 mg, most preferably less than 100 mg, particularly preferred less than 50 mg, and particularly preferred less than 10 mg of the pigments are soluble in 1 l of solvent like dimethylformamid, at 20° C. It is self-evident, that the solubility are higher at increasing temperatures and depend on the choice of a solvent.

Under the aspects of the invention, wherein there is a loss of a small molecule(s), usually a gas, upon deliberation of the pigment from its precursor, the actual amount of precursor may exceed the limit of 10 weight percent prescribed for the pigment itself.

In the context of this invention, the term "dissolved" means that a molecule exists as a free and isolated entity in a given surrounding or matrix, preferably in such a way, that it is disengaged from any interactions between molecules of the same species, i.e. it is entirely surrounded by matrix molecules. Usually the matrix can be a liquid organic solvent or a solid material such as a polymer or another fluorescent material (host), which possesses a different chemical structure. The concentration limits for molecules in the dissolved state in general depend strongly on the associative nature between the molecule and the matrix medium, and/or the intrinsic cohesive forces that exist between the guest molecules in question. Correspondingly, it is impossible to define universal ranges for preferred concentrations, and therefore, usually must be treated on an ad hoc basis, e.g. by a few simple experiments.

The weight ratio of (host plus pigment):polymer matrix is dependent on the actual practical application, hence there are no well defined preferred ratios, other than the broad range 90:10 to 1:999. In certain applications where both color strength and fluorescence are required, then the preferred ratios of (host plus pigment) to polymer matrix are 20:80 to 90:10, preferably 50:50 to 90:10 and more preferably 80:20 to 90:10. In circumstances where fluorescence is desired but color strength is not required, then the preferred ratio (host plus pigment) to polymer matrix are 20:80 to 1:999, more preferably 10:90 to 1:999 and more preferably 5:95 to 1:999.

The ratio of host to pigment may be for example 10000:1 to 10:1. Preferred ranges are 5000:1 to 10:1, more preferably 1000:1 to 20:1.

In the context of the invention isolation means evaporation of a solvent, precipitation from a solution (for example through addition of a non-solvent under vigorous stirring), freeze-drying or precipitation through polymerization of polymerisable monomers or oligomers, preferably under vigorous stirring.

Suitable inert solvents are for example protic-polar and aprotic solvents, which may be used alone or in an admixture of at least two solvents. Examples are: water, alcohols (methanol, ethanol, propanol, butanol), ethyleneglycolmonomethyl- or -monoethylether, ethers (dibutylether, tetrahydrofuran, dioxane, ethyleneglycol dimethylether, ethyleneglycoldiethylether, diethyleneglycoldiethylether, triethyleneglycoldimethylether), halogenated hydrocarbons (methylenchloride, chloroform, 1,2-dichloroethane, 1,1,1-trichlororethane, 1,1,2,2-tetrachloroethane), carboxylic esters and lactones (acetic acid ethylester, propionic acid methylester, benzoic acid ethylester, 2-methoxyethylacetate, γ-butyrolactone, δ-valerolactone, pivalolactone), carboxylic acid amides and lactames; N,N-dimethylformamide, N,N-diethylformamide, N,N-dimethylacetamide, tetramethylurea, hexamethylphosphorous acidtriamide, γ-butyrolactame, ε-caprolactame, N-methylpyrrolidone, N-acetylpyrrolidone, N-methylcaprolactame; sulfoxides (dimethylsulfoxide), sulfones (dimethylsulfone, diethylsulfone, trimethylenesulfone, tetramethylenesulfone), tertiary amines (N-methylpiperidine, N-methylmorpholine), aliphatic and aromatic hydrocarbons like petroleumether, pentane, hexane, cyclohexane, methylcyclohexane, benzene or substituted benzenes (chlorobenzol, o-dichlorobenzene, 1,2,4-trichlorobenzene, nitrobenzene, toluene, xylene) and nitriles (acetonitrile, propionitrile, benzenenitrile, phenylacetonitrile), ketones (acetone, methyl-isobutyl-ketone).

The precipitation process may be carried-out by a variety of means. When the pigment precursors, the host chromophores and polymers possess solubilities affording the desired weight range in the final composition, the precipitation may be completed by adding the solution to a large excess of non-solvent, preferably under vigorous stirring, filtering off then the precipitate and removing the non-solvent, preferably by drying the solid at elevated temperatures and more preferably under vacuum. Another possibility is to evaporate the solvent under vacuum and/or elevated temperatures.

Another preferred embodiment of the present invention is to isolate the soluble host chromophores, pigment precursors and optionally polymers is freeze-drying, as a steady state of host, pigment precursor and the solvent is generated by freezing the solution, which contains the host chromophores, pigment precursors and optionally polymers in an homogeneous distribution. This state usually is maintained upon removal of the solvent by freeze-drying.

Another embodiment of the present invention is to dissolve the pigment precursors and optionally the host chromophores in a suitable solvent and to add it to a polymer gel (polymer swollen with a solvent). The host chromophores and pigment precursors usually penetrate into the gel. Removal of the solvent and drying in general generates a composition from which the pigment can be deliberated to afford a composition according to the invention.

Another preferred embodiment of the present inevntion is to mill together host chromophores and pigment precursors using a ball mill. Due to the high shearing forces the pigment precursor preferably penetrates into the host chromophore to form a solid solution from which the pigment can be generated.

Another preferred embodiment of the present invention is to mix together the host chromophores, the pigment precursor and optionally a polymer, by melt-mixing them at temperatures below the decomposition temperatures of the components, optionally under pressure.

Another preferred embodiment of the present invention is to dissolve a pigment precursor and optionally a host chromophore in polymer precursors like polymerisable monomers or oligomers with or without solvent and to polymerize the mixture in known manner like bulk, solution or emulsion polymerization, thereby forming a polymer solid solution. By using emulsion polymerization, highly desired and finely divided particles can be obtained.

In the context of the invention generation of the pigment from the pigment precursor means removing protecting groups linked to the corresponding pigment. The protecting groups may additionally have the function to solubilize the insoluble pigment. The removal of protecting groups may be achieved by chemical means like acids or bases, or catalysts present in the composition, by radiation, by heating, or a combination of these methods. A preferred method is heating, whereby addition of small amounts of acid, base and or catalysts may assist to facilitate the forming of the pigment.

To produce the compositions according to the invention from the above solid solutions (precipitates) the pigment preferably is deliberated from the pigment precursor under the action of heat, such that it does not migrate to form undesired non-fluorescent pigment particles. To avoid the migration preferably a temperature is selected according to the decomposition temperature of the pigment precursor and the thermal properties of the host chromophores and the polymers used.

Preferably, the temperature is below the decomposition temperatures of the host chromophore and the polymer. In addition, it is preferred, the temperature being also below the melting temperatures of the host chromophore and the polymer to avoid migration of the generated pigment. Further, preferably the temperature is above the decomposition temperature of the pigment precursor, too.

In general the mobility of the deliberated pigment is low at temperatures of about 100° C. or less, so that a broad range of polymers or host chromophores can be selected when those temperatures are employed. The temperature range for the heat treatment of the solid solution may be for example at least 50° C. using irradiation and or acids, and may be below the melting or softening (or glass transition temperatures) of the host chromophores and polymers respectively, when higher temperatures like more than 100° C. or 120° C. are employed, due to a higher mobility of the deliberated pigment. In practical terms the temperature may be from 50 to 250° C., preferably 70 to 220° C., more preferably 80 to 200° C., and most preferably 100 to 180° C.

When a polymer matrix is used the selected decomposition temperature may also depend on the softening or glass transition temperature of the polymers, to avoid the migration of the generated pigment molecules, as it may lead to the formation of undesired nanosize pigment particles. It was found that the heating temperature preferably is chosen about or slightly above the softening or glass transition temperatures, particularly when short and optionally repeated heating times are employed. Short and spared heating times can be achieved for example with microwaves or heat radiation. These methods can also be employed to polymers with low glass transition temperatures like polyolefines or rubbers.

The composition generated by the process of the invention contains pigment usually in the molecularly dissolved state, whereby the pigment itself is insoluble in a solvent or polymer matrix. The compositions according to the invention thus usually do not show the typical color of the pigment in compositions containing a polymer matrix and only the pigment, or the typical mixed color in compositions containing a host chromophore optionally together with a polymer matrix. The color of the compositions can be used therefore as a means of control in the decomposition of the pigment precursor. Preferably, these compositions are prepared using soluble pigment precursors.

Suitable pigment precursors are well known and described for example in EP-A-0 648 770 and EP-A-0 648 817. Preferred pigments are those containing NH-groups, wherein the hydrogen is replaced by a protecting group. The protecting group in general has the functions to solublize the pigment and usually can be removed by various means, preferably by heat. Preferred protecting groups correspond to the formulae I and Ia,

$$—C(O)—OR_1 \qquad (I),$$

$$—C(O)—NHR_1 \qquad (Ia),$$

wherein $R_1$ means $C_1$ to $C_{20}$ alkyl, $C_2$ to $C_{20}$ alkenyl or $C_3$ to $C_{20}$ alkynyl; or phenyl, benzyl, 1-phenyl-1-ethyl, or 2-phenyl-2,2-propylidene, which are unsubstituted or substituted with OH, F, Cl, Br, $C_1$ to $C_4$ alkyl, $C_1$ to $C_4$ halogenalkyl, $C_1$ to $C_4$ alkoxy, $C_1$ to $C_4$ alkylthio, phenyl or $C_1$ to $C_{12}$ alkylphenyl.

The alkyl, alkenyl or alkynyl may be linear or branched. Alkyl contains preferably 1 to 18, more preferably 1 to 14 and particularly preferred 1 to 12 carbon atoms. The alkyl is preferably branched at the α-position with one and more, preferably two, $C_1$ to $C_4$ alkyl groups, especially preferred methyl groups. Some examples are i-propyl, t-butyl, but-2-yl, 2-methylbut-2-yl, and 1,1,2,2-tetramethyleth-1-yl.

Alkenyl contains preferably 2 to 18, more preferably 2 to 14 and particularly preferred 2 to 12 carbon atoms. The ethylenic group is preferably located at the 2- or 3-position, related to the carbon/oxygen or carbon/nitrogen linkage in formulae I and Ia. Branched alkenyl is preferably branched at the α-position with one and more, preferably two, $C_1$ to $C_4$ alkyl groups, particularly preferred methyl groups.

Alkynyl contains preferably 3 to 18, more preferably 3 to 14 and particularly preferred 3 to 12 carbon atoms. The ethylinic group is preferably located at the 2- or 3-position, related to the carbon/oxygen or carbon/nitrogen linkage in formulae I and Ia. Branched alkynyl is preferably branched at the α-position with one and more, preferably two, $C_1$ to $C_4$ alkyl groups, particularly preferred methyl groups.

The pigments may be selected from the group consisting of nitrogen containing organic pigments like quinacridones, anthraquinones, perylenes, indigos, quinophthalones, isoindolinones, phthalocyanines, diketo- and dithioketopyrrolopyrroles, azo pigments and mixtures thereof.

More preferred are organic pigments selected from the group consisting of quinacridones, perylenes and diketopyrrolopyrroles.

The quinacridones may correspond to the formula II,

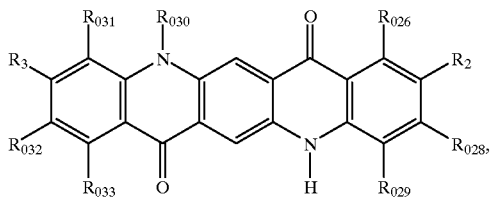

(II)

wherein

R$_2$, R$_3$, R$_{026}$ to R$_{029}$ and R$_{031}$ to R$_{033}$ are independently from one another H, C$_1$ to C$_6$ alkyl, C$_1$ to C$_6$ alkoxy, F, Cl, Br, CN, NO$_2$, or —NR$_{021}$R$_{022}$, wherein R$_{021}$ and R$_{022}$ independently from one another are H, C$_1$ to C$_{20}$ alkyl, phenyl, C$_1$ to C$_{12}$ alkylphenyl, benzyl or C$_1$ to C$_{12}$ alkylbenzyl, or R$_{021}$ and R$_{022}$ together mean tetramethylene, pentamethylene or —CH$_2$CH$_2$—O—CH$_2$CH$_2$—; or two neighbored residues of R$_2$, R$_{026}$ to R$_{029}$ and/or R$_3$, R$_{031}$ to R$_{033}$ together with carbon atoms, to which they are linked, a 5- or 6-membered aliphatic, heteroaliphatic, aromatic or heteroaromatic ring, whereby the herteroatoms are selected from the group of —O—, —S— and N; and R$_{030}$ is H, C$_1$ to C$_{18}$ alkyl, C$_2$ to C$_{18}$ alkenyl, C$_2$ to C$_{18}$ alkynyl, phenyl, benzyl, C$_1$ to C$_6$ alkylphenyl, C$_1$ to C$_6$ alkylbenzyl or R$_{036}$—O—C(O)—, wherein R$_{036}$ means C$_1$ to C$_{18}$ alkyl, C$_2$ to C$_{18}$ alkenyl, C$_2$ to C$_{18}$ alkynyl, phenyl, benzyl, C$_1$ to C$_6$ alkylphenyl, or C$_1$ to C$_6$ alkylbenzyl.

Perylenes are for example described in U.S. Pat. No. 4,446,324 and U.S. Pat. No. 5,470,502. Preferred examples are those perylenes of formulae III and IV,

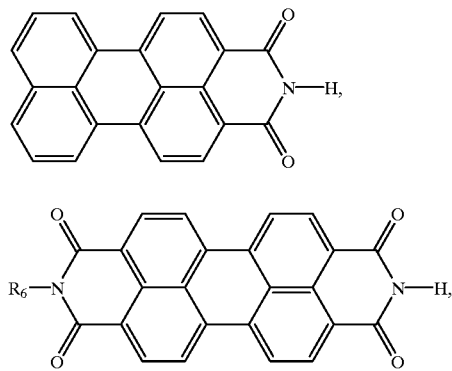

(III)

(IV)

wherein

R$_6$ is H, C$_1$ to C$_4$ alkyl, C$_2$ to C$_4$ alkenyl, C$_2$ to C$_4$ alkynyl, phenyl, benzyl, C$_1$ to C$_6$ alkylphenyl, C$_1$ to C$_6$ alkylbenzyl or R$_1$—O—C(O)—, wherein R$_1$ means C$_1$ to C$_{18}$ alkyl, C$_2$ to C$_{18}$ alkenyl, C$_2$ to C$_{18}$ alkynyl, phenyl, benzyl, C$_1$ to C$_6$ alkylphenyl, or C$_1$ to C$_6$ alkyl benzyl, and which are unsubstituted or substituted with halogen, preferably F, Cl or Br, CN, C$_1$ to C$_4$ alkyl, C$_1$ to C$_4$ alkoxy, or phenyl or phenoxy, which are unsubstituted or substituted with halogen, preferably F, Cl or Br, CN, C$_1$ to C$_4$ alkyl, C$_1$ to C$_4$ alkoxy.

Examples for diketopyrrolo-pyrroles correspond to the formula V,

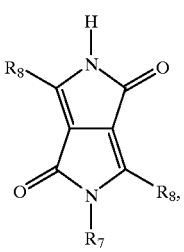

(V)

wherein the R$_8$ independently from one another are H, halogen, or phenyl which is unsubstituted or substituted with C$_1$ to C$_6$ alkyl, C$_1$ to C$_6$ alkoxy, phenyl, C$_1$ to C$_4$ alkylphenyl, F, Cl, Br, CN, NO$_2$, or —NR$_{21}$R$_{22}$, wherein R$_{21}$, and R$_{22}$ independently from one another are H, C$_1$ to C$_{20}$ alkyl, phenyl, C$_1$ to C$_{12}$ alkylphenyl, benzyl or C$_1$ to C$_{12}$ alkylbenzyl, or R$_{21}$ and R$_{22}$ together mean tetramethylene, pentamethylene or —CH$_2$CH$_2$—O—CH$_2$CH$_2$—; and R$_7$ means H, C$_1$ to C$_{18}$ alkyl, C$_2$ to C$_{18}$ alkenyl, C$_2$ to C$_{18}$ alkynyl, phenyl, benzyl, C$_1$ to C$_6$ alkylphenyl, or C$_1$ to C$_6$alkylbenzyl, or R$_1$—O—C(O)—, wherein R$_1$ means C$_1$ to C$_{18}$ alkyl, C$_2$ to C$_{18}$ alkenyl, C$_2$ to C$_{18}$ alkynyl, phenyl, benzyl, C$_1$ to C$_6$ alkylphenyl, or C$_1$ to C$_6$ alkylbenzyl.

The pigments are well known or can be prepared according to known methods in the art (see for example "Industrial Organic Pigments" by W. Herbst and K. Hunger, published by VCH (1993)).

Host chromophores can be selected from a broad range of chromophores, so long as (i) they emit solid-state fluorescence, and that their emission spectra overlap with the absorption spectrum of the corresponding guest pigment in the system, and (ii) they dissolve a pigment precursor, and one or both are soluble in a solvent and optionally in a polymer. Appropriate host chromophores are for example described in WO 93/23492.

The term host chromophore may be for example selected from the group consisting of fluorescent anthracenes, oxazoles, pyrenes, coumarines, fluoresceines, rhodamines, perylenes, perinones, isoindolones and metal complexes consisting of metals and organic ligands. Examples for organic ligands are quinolines, phenanthrolines, bipyridines, azos and azomethines. Some specific examples of metal complexes are tris(8-hydroxyquinolinate) aluminum, bis(8-hydroxyquinolinate) beryllium, bis(8-hydroxyquinolinate) magnesium, bis( 8-hydroxyquinolinate) zinc, bis(10-hydroxybenzo[h]quinolinate) beryllium, tris(1,3-diphenyl-1,3-propanediono)(monophenanthroline) europium and (N,N'-disalicylidene-1,6-hexanediaminate) zinc.

The host chromophore may be unsubstituted or substituted with F, Cl, Br, I, —CN, —NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to $C_{12}$ cycloalkyl-SO— or —$SO_2$, $C_6$ to $C_{18}$ aryl-SO— or —$SO_2$, $C_5$ to $C_{17}$ heteroaryl-SO— or —$SO_2$, $C_3$ to $C_{12}$ cycloalkylalkyl-SO— or —$SO_2$, $C_6$ to $C_{18}$ aralkyl-SO— or —$SO_2$, $C_5$ to $C_{17}$ heteroaralkyl-SO— or —$SO_2$, secondary amines with 2 to 30 carbon atoms, and alkoxyalkyl with 2 to 20 carbon atoms.

The cyclic aliphatic and aromatic residues (substituents) may be also substituted, for example with F, Cl, Br, I, —CN, —$NO_2$, $C_1$ to $C_{18}$ alkyl, $C_3$ to $C_{12}$ cycloalkyl, $C_6$ to $C_{18}$ aryl, $C_3$ $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy. The alkyl substituent may be linear or branched and may be substituted with a halogen like F or Cl.

Examples of substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-$SO_2$, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

The number of substituents is arbitrary and depends essentially upon synthetic possibilities and the desired optical properties pertaining to fluorescence and absorption.

A preferred group of host chromophores is selected from anthracenes, perylenes, phtaloperinones, benzoimidazoisoindolones and metal complexes.

Particularly preferred host chromophores are 8-hydroxyquinoline aluminums and benzo[4,5]imidazo[2,1-a]isoindol-11-ones, the latter ones being most preferred.

The benzoimidazoisoindolones may correspond to the formula VI

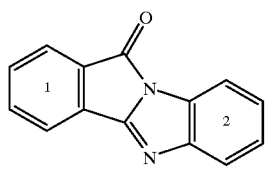

(VI)

wherein
the neighboring carbon atoms of the benzene rings 1 and 2 are uncondensed or condensed with benzene rings, heteroaromatic rings, aliphatic rings, or hetroaliphatic rings, and wherein the benzene rings 1 or 2 or both, the condensed ring moieties or all are unsubstituted or substituted with organic groups and/or halogen atoms.

The groups forming a condensed ring are preferably selected from the group consisting of bivalent residues of formulae —CH=CH—CH=CH—, —CH=CH—N=CH—, —CH=CH—CH=N—, —CH=N—CH=N—, —CH=CH—$NR_9$—, —CH=N—$CH_2$—, —CH=CH—S—, —CH=CH—O—, —$(CH_2)_3$—, —$(CH_2)_4$—, —$CH_2$—$CH_2$—$NR_9$—$CH_2$—, —$CH_2$—$CH_2$—$CH_2$—$NR_9$—, —$CH_2$—$CH_2$—$CH_2$—O—, —$CH_2$—$CH_2$—S—$CH_2$—, —$CH_2$—$CH_2$—O—$CH_2$—, —$CH_2$—$CH_2$—$CH_2$—S—, —$CH_2$—O—$CH_2$—, —$CH_2$—$CH_2$—O—, —$CH_2$—S—$CH_2$—, and —$CH_2$—$CH_2$—S—, wherein $R_9$ is H or an organic substituent, and the bivalent residues are unsubstituted or substituted with an organic group.

$R_9$ as organic substituent may be linear or branched $C_1$ to $C_{20}$ alkyl, $C_5$ to $C_7$ cycloalkyl, benzyl or $R_{10}$—C(O)—, wherein $R_{10}$ is $C_1$ to $C_{20}$ alkyl, which is unsubstituted or substituted with F, Cl or $C_1$ to $C_{12}$ alkoxy, or $C_5$ to $C_7$ cycloalkyl, phenyl or benzyl, which are unsubstituted or substituted with F, Cl, $C_1$ to $C_{12}$ alkyl, or $C_1$ to $C_{12}$ alkoxy.

Preferred examples for $R_9$ are H, methyl, ethyl, propyl, butyl, pentyl, hexyl, benzyl, methylbenzyl, dimethylbenzyl, acetyl, propionyl, butyroyl, benzyl-C(O)—, phenyl-C(O)—, toluyl-C(O)—, mono-, di- or tri-chloroacetyl, and mono-, di- or tri-fluoroacetyl, mono- and dichlorophenyl-C(O)—.

The organic group substituent may be selected from the group consisting of halogen, —CN, —$NO_2$, $C_1$ to $C_{18}$ alkyl, $C_2$ to $C_{18}$ alkenyl, $C_2$ to $C_{18}$ alkynyl, $C_1$ to $C_{18}$ hydroxyalkyl, $C_1$ to $C_{18}$ halogenalkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —$SO_2$, $C_3$ to $C_{12}$ cycloalkyl-SO— or —$SO_2$, $C_6$ to $C_{18}$ aryl-SO— or —$SO_2$, $C_5$ to $C_{17}$ heteroaryl-SO— or —$SO_2$, $C_3$ to $C_{12}$ cycloalkylalkyl-SO— or —$SO_2$, $C_6$ to $C_{18}$ aralkyl-SO— or —$SO_2$, $C_1$ to $C_{18}$ alkyl-CO—, $C_3$ to $C_{12}$ cycloalkyl-CO—, $C_6$ to $C_{18}$ aryl-CO—, $C_5$ to $C_{17}$ heteroaryl-CO—, $C_3$ to $C_{12}$ cycloalkylalkyl-CO—, $C_6$ to $C_{18}$ aralkyl-CO—, $C_5$ to $C_{17}$ heteroaralkyl-CO—, —$NR_{11}R_{12}$, alkoxyalkyl with 2 to 20 carbon atoms, polyoxyalkylene-$OR_{14}$, —X—$(R_{13})_k$—C(O)—$NR_{11}R_{12}$, —X—$(R_{13})_k$—C(O)—$OR_{14}$, —X—$(R_{13})_k$—$SO_2$—$OR_{14}$, —X—$(R_{13})_k$—$SO_2$—$NR_{11}R_{12}$, —NH—C(O)—$R_{14}$ and —O—C(O)—$R_{14}$, wherein $R_{11}$ and $R_{12}$ independently from one another mean H, $C_1$ to $C_{20}$ alkyl, cyclopentyl, cyclohexyl, phenyl, benzyl, $C_1$ to $C_{12}$ alkylphenyl or $C_1$ to $C_{12}$ alkylbenzyl, or $R_{11}$ and $R_{12}$ together mean tetramethylene, pentamethylene, or the groups —$CH_2$—$CH_2$—O—$CH_2$—$CH_2$— or —$CH_2$—$CH_2$—$NR_{15}$—$CH_2$—$CH_2$—, $R_{13}$ is $C_1$ to $C_{12}$ alkylene, phenylene or benzylene, $R_{14}$ means H, $C_1$ to $C_{20}$ alkyl, cyclopentyl, cyclohexyl, phenyl, benzyl, $C_1$ to $C_{12}$ alkylphenyl or $C_1$ to $C_{12}$alkylbenzyl, $R_{15}$ is H or $C_1$ to $C_4$ alkyl, X is a direct bond, —O— or S, k is 0 or 1, and and the salts of the acids.

Preferred salts are the alkaline metal and earth alkaline metal salts, e.g. from Li, Na, K, Mg, Ca, Sr, Ba.

The cyclic aliphatic and aromatic residues (substituents for the organic group) may be also substituted, for example with F, Cl or Br, —CN, —$NO_2$, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy.

In the context of the invention the alkyl substituent may be linear or branched and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention the organic group substituent halogen may be F, Cl, Br or I and is preferably F or Cl.

In the context of the invention the organic group substituent alkenyl may be linear or branched and contains preferably 2 to 12 C-atoms, more preferably 2 to 8 C-atoms, most preferably 2 to 6 C-atoms and particularly preferred 2 to 4 C-atoms. Some examples are vinyl, allyl, methylvinyl, but-1-ene-4-yl, but-2-ene-4-yl, but-3-ene-4-yl, 3-methyl-prop-1-ene-3-yl, and the isomers of pentenyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

In the context of the invention the alkynyl substituent may be linear or branched and contains preferably 2 to 12 C-atoms, more preferably 2 to 8 C-atoms, most preferably 2 to 6 C-atoms and particularly preferred 2 to 4 C-atoms. Some examples are ethinyl, crotonyl, methylethenyl, but-1-ine-4-yl, but-2-ine-4-yl, but-3-ine-4-yl, 3-methyl-prop-1-in-3-yl, and the isomers of pentinyl, hexinyl, heptinyl, octinyl, noninyl, decinyl, undecinyl, dodecinyl, tridecinyl, tetradecinyl, pentadecinyl, hexadecinyl, heptadecinyl and octadecinyl.

In the context of the invention the hydroxyalkyl substituent may be linear or branched and contain preferably 1 to 12 C-atoms, more preferably 1 to 8 C-atoms, most preferably 1 to 6 C-atoms and particularly preferred 1 to 4 C-atoms. Some examples are hydroxymethyl, hydroxyethyl, n- or i-hydroxypropyl, n-, i- or t-hydroxybutyl, and the isomers of hydroxypentyl, hydroxyhexyl, hydroxyheptyl, hydroxyoctyl, hydroxynonyl, hydroxydecyl, hydroxyundecyl, hydroxydodecyl, hydroxytridecyl, hydroxytetradecyl, hydroxypentadecyl, hydroxyhexadecyl, hydroxyheptadecyl and hydroxyoctadecyl.

In the context of the invention the organic group substituent halogenalkyl may be linear or branched and contain preferably 1 to 12 C-atoms, more preferably 1 to 8 C-atoms, most preferably 1 to 6 C-atoms and particularly preferred 1 to 4 C-atoms. The halogen may be F, Cl, Br or I, and is preferably F and Cl. Some examples are chloromethyl, dichloromethyl, trichloromethyl, fluoromethyl, difluoromethyl, trifluoromethyl, chloroethyl, n- or i-chloropropyl, n-, i- or t-chlorobutyl, perfluoroethyl and perfluorobutyl.

In the context of the invention the cycloalkyl substituent contains preferably 4 to 8 and more preferred 5 to 7 ring carbon atoms. Examples are cyclopropyl, cyclobutyl, cyclopentyl, cyclohexyl, cycloheptyl, cyclooctyl and cyclododecyl. Preferred groups are cyclopentyl and cyclohexyl.

In the context of the invention the aryl substituent may be naphthyl or preferably phenyl.

In the context of the invention the heteroaryl substituent contains preferably 5 or 6 ring atoms and preferably 1 to 3, more preferably 1 or 2 heteroatoms selected from group consisting of O, S and N. Some examples are pyridinyl, pyrimidinyl, furanyl, pyrrolyl and thiophenyl.

In the context of the invention the cycloalkyl-alkyl substituent is preferably cycloalkyl-methyl or -ethyl, and cycloalkyl means preferably cyclopentyl or cyclohexyl.

In the context of the invention the aralkyl substituent is preferably arylmethyl or -ethyl, and aryl means preferably phenyl or naphthyl. Some examples are benzyl, phenylethyl and naphthylmethyl.

In the context of the invention the heteroaralkyl substituent is preferably heteroarylmethyl or -ethyl, and the heteroaryl contains preferably 5 or 6 ring atoms and preferably 1 to 3, more preferably 1 or 2 heteroatoms selected from group consisting of O, S and N. Some examples are pyridinylmethyl or -ethyl, pyrimidinyl, furanylmethyl, pyrrolylmethyl and thiophenylmethyl.

In the context of the invention the organic group substituent alkoxy may be linear or branched and contains preferably 1 to 12 C-atoms, more preferably 1 to 8 C-atoms, most preferably 1 to 6 C-atoms and particularly preferred 1 to 4 C-atoms. Some examples are methoxy, ethoxy, n- or i-propoxy, n-, i- or t-butoxy, and the isomers of pentoxy, hexoxy, heptoxy, octoxy, nonyloxy, decyloxy, undecyloxy, dodecyloxy, tridecyloxy, tetradecyloxy, pentadecyloxy, hexadecyloxy, heptadecyloxy and octadecyloxy.

In the context of the invention the cycloalkyloxy substituent contains preferably 4 to 8 and more preferred 5 to 7 carbon ring atoms. Examples are cyclopropyloxy, cyclobutyloxy, cyclopentyloxy, cyclohexyloxy, cycloheptyloxy, cyclooctyloxy and cyclododecyloxy. Preferred groups are cyclopentyloxy and cyclohexyloxy.

In the context of the invention the aryloxy substituent may be naphthyloxy or preferably phenyloxy.

In the context of the invention the heteroaryloxy substituent contains preferably 5 or 6 ring atoms and preferably 1 to 3, more preferably 1 or 2 heteroatoms selected from group consisting of O, S and N. Some examples are pyridinyloxy, pyrimidinyloxy, furanyloxy, pyrrolyloxy and thiophenyloxy.

In the context of the invention the cycloalkyl-alkyloxy substituent is preferably cycloalkyl-methyloxy or -ethyloxy, and cycloalkyl means preferably cyclopentyl or cyclohexyl.

In the context of the invention aralkyloxy substituent is preferably arylmethyloxy or -ethyloxy, and aryl means preferably phenyl or naphthyl. Some examples are benzyloxy, phenylethyloxy and naphthylmethyloxy.

In the context of the invention the heteroaralkyloxy substituent is preferably heteroarylmethyl or -ethyl, and the heteroaryl contains preferably 5 or 6 ring atoms and preferably 1 to 3, more preferably 1 or 2 heteroatoms selected from group consisting of O, S and N. Some examples are pyridinylmethyloxy or -ethyloxy, pyrimidinyloxy, furanylmethyloxy, pyrrolylmethyloxy and thiophenylmethyloxy.

In the context of the invention the alkylthio substituent may be linear or branched and contains preferably 1 to 12 C-atoms, more preferably 1 to 8 C-atoms, most preferably 1 to 6 C-atoms and particularly preferred 1 to 4 C-atoms. Some examples are methylthio, ethylthio, n- or i-propylthio, n-, i- or t-butylthio, and the isomers of pentylthio, hexylthio, heptylthio, octylthio, nonylthio, decylthio, undecylthio, dodecylthio, tridecylthio, tetradecylthio, pentadecylthio, hexadecylthio, heptadecylthio and octadecylthio.

In the context of the invention the cycloalkyl substituent contains preferably 4 to 8 and more preferred 5 to 7 ring carbon atoms. Examples are cyclopropylthio, cyclobutylthio, cyclopentylthio, cyclohexylthio, cycloheptylthio, cyclooctylthio and cyclododecylthio. Preferred. groups are cyclopentylthio and cyclohexylthio.

In the context of the invention the arylthio substituent may be naphthylthio or preferably phenylthio.

In the context of the invention the heteroarylthio substituent contains preferably 5 or 6 ring atoms and preferably 1 to 3, more preferably 1 or 2 heteroatoms selected from group consisting of O, S and N. Some examples are pyridinylthio, pyrimidinylthio, furanylthio, pyrrolylthio and thiophenylthio.

In the context of the invention the cycloalkyl-alkylthio substituent is preferably cycloalkyl-methylthio or -ethylthio, and cycloalkyl means preferably cyclopentyl or cyclohexyl.

In the context of the invention the aralkylthio substituent is preferably arylmethylthio or -ethylthio, and aryl means preferably phenyl or naphthyl. Some examples are benzylthio, phenylethylthio and naphthylmethylthio.

In the context of the invention the heteroaralkylthio substituent is preferably heteroarylmethylthio or -ethylthio, and the heteroaryl contains preferably 5 or 6 ring atoms and preferably 1 to 3, more preferably 1 or 2 heteroatoms selected from group consisting of O, S and N. Some examples are pyridinylmethylthio or -ethylthio, pyrimidinylthio, furanylmethylthio, pyrrolylmethylthio and thiophenylmethylthio.

In the context of the invention the alkyl-SO— or —SO$_2$— substituent may be linear or branched and contains preferably 1 to 12 C-atoms, more preferably 1 to 8 C-atoms, most preferably 1 to 6 C-atoms and particularly preferred 1 to 4 C-atoms. Some examples are methyl-SO— or —SO$_2$—, ethyl-SO— or —SO$_2$—, n- or i-propyl-SO— or —SO$_2$—, n-, i- or t-butyl-SO— or —SO$_2$—, and the isomers of pentyl-SO— or —SO$_2$—, hexyl-SO— or —SO$_2$—, heptyl-SO— or —SO$_2$—, octyl-SO— or —SO$_2$—, nonyl-SO— or —SO$_2$—, decyl-SO— or —SO$_2$—, undecyl-SO— or —SO$_2$—, dodecyl-SO— or —SO$_2$—, tridecyl-SO— or —SO$_2$—, tetradecyl-SO— or —SO$_2$—, pentadecyl-SO— or —SO$_2$—, hexadecyl-SO— or —SO$_2$—, heptadecyl-SO— or —SO$_2$— and octadecyl-SO— or —SO$_2$—.

In the context of the invention the cycloalkyl-SO— or —SO$_2$— substituent contains preferably 4 to 8 and more preferred 5 to 7 ring carbon atoms. Examples are cyclopropyl-SO— or —SO$_2$—, cyclobutyl-SO— or —SO$_2$—, cyclopentyl-SO— or —SO$_2$—, cyclohexyl-SO— or —SO$_2$— cycloheptyl-SO— or —SO$_2$—, cyclooctyl-SO— or —SO$_2$— and cyclododecyl-SO— or —SO$_2$—. Preferred groups are cyclopentyl-SO— or —SO$_2$— and cyclohexyl-SO— or —SO$_2$—.

In the context of the invention the aryl-SO— or —SO$_2$— substituent may be naphthyl-SO— or —SO$_2$— or preferably phenyl-SO— or —SO$_2$—.

In the context of the invention the heteroaryl-SO— or —SO$_2$— substituent contains preferably 5 or 6 ring atoms and preferably 1 to 3, more preferably 1 or 2 heteroatoms selected from group consisting of O, S and N. Some examples are pyridinyl-SO— or —SO$_2$—, pyrimidinyl-SO— or —SO$_2$—, furanyl-SO— or —SO$_2$—, pyrrolyl-SO— or —SO$_2$— and thiophenyl-SO— or —SO$_2$—.

In the context of the invention cycloalkyl-alkyl-SO— or —SO$_2$— the substituent is preferably cycloalkyl-methyl-SO— or —SO$_2$— or -ethyl-SO— or —SO$_2$—, and cycloalkyl means preferably cyclopentyl or cyclohexyl.

In the context of the invention the aralkyl-SO— or —SO$_2$— substituent is preferably arylmethyl-SO— or —SO$_2$— or -ethyl-SO— or —SO$_2$—, and aryl means preferably phenyl-SO— or —SO$_2$— or naphthyl-SO— or —SO$_2$—. Some examples are benzyl-SO— or —SO$_2$—, phenylethyl-SO— or —SO$_2$—and naphthylmethyl-SO— or —SO$_2$—.

In the context of the invention the heteroaralkyl-SO— or —SO$_2$— substituent is preferably heteroarylmethyl-SO— or —SO$_2$— or -ethyl-SO— or —SO$_2$—, and the heteroaryl contains preferably 5 or 6 ring atoms and preferably 1 to 3, more preferably 1 or 2 heteroatoms selected from group consisting of O, S and N. Some examples are pyridinylmethyl-SO— or —SO$_2$— or -ethyl-SO— or —SO$_2$—, pyrimidinyl-SO— or —SO$_2$—, furanylmethyl-SO— or —SO$_2$—, pyrrolylmethyl-SO— or —SO$_2$— and thiophenylmethyl-SO— or —SO$_2$—.

In the context of the invention the alkyl-CO— substituent may be linear or branched and contains preferably 1 to 12 C-atoms, more preferably 1 to 8 C-atoms, most preferably 1 to 6 C-atoms and particularly preferred 1 to 4 C-atoms. Some examples are methyl-CO—, ethyl-CO—, n- or i-propyl-CO—, n-, i- or t-butyl-CO—, and the isomers of pentyl-CO—, hexyl-CO—, heptyl-CO—, octyl-CO—, nonyl-CO—, decyl-CO—, undecyl-CO—, dodecyl-CO—, tridecyl-CO—, tetradecyl-CO—, pentadecyl-CO—, hexadecyl-CO—, heptadecyl-CO— and octadecyl-CO—.

In the context of the invention the cycloalkyl-CO— substituent contains preferably 4 to 8 and more preferred 5 to 7 ring carbon atoms. Examples are cyclopropyl-CO—, cyclobutyl-CO—, cyclopentyl-CO—, cyclohexyl-CO—, cycloheptyl-CO—, cyclooctyl-CO— and cyclododecyl-CO—. Preferred groups are cyclopentyl-CO— and cyclohexyl-CO—.

In the context of the invention the aryl-CO— substituent may be naphthyl-CO— or preferably phenyl-CO—.

In the context of the invention the heteroaryl substituent contains preferably 5 or 6 ring atoms and preferably 1 to 3, more preferably 1 or 2 heteroatoms selected from group consisting of O, S and N. Some examples are pyridinyl, pyrimidinyl, furanyl, pyrrolyl and thiophenyl.

In the context of the invention the cycloalkyl-alkyl-CO— substituent is preferably cycloalkyl-methyl-CO— or -ethyl-CO—, and cycloalkyl means preferably cyclopentyl or cyclohexyl.

In the context of the invention the aralkyl-CO— substituent is preferably arylmethyl-CO— or —ethyl-CO—, and aryl means preferably phenyl-CO— or naphthyl-CO—. Some examples are benzyl-CO—, phenylethyl-CO— and naphthylmethyl-CO—.

In the context of the invention the heteroaralkyl-CO— substituent is preferably hetero arylmethyl-CO— or -ethyl-CO—, and the heteroaryl contains preferably 5 or 6 ring atoms and preferably 1 to 3, more preferably 1 or 2 heteroatoms selected from group consisting of O, S and N. Some examples are pyridinylmethyl-CO— or -ethyl-CO—, pyrimidinyl-CO—, furanylmethyl-CO—, pyrrolylmethyl-CO— and thiophenylmethyl-CO—.

In the context of the invention the alkoxyalkyl substituent contains preferably in total 2 to 12, more preferably 2 to 8 and most preferably 2 to 6 carbon atoms. The alkoxy may contain 1 to 4 carbon atoms. Some examples are methoxyethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, ethoxyhexyl, propoxymethyl and butoxymethyl.

In the context of the invention the polyoxyalkylene-O-R$_6$ substituent preferably contains 2 to 12 and more preferably 2 to 6 oxyalkylene units, wherein alkylene is preferably ethylene, 1,2- or 1,3-propylene or 1,2-, 1,3- or 1,4-butylene. R$_6$ is preferably H or C$_1$ to C$_4$ alkyl.

In the context of the invention when R$_{11}$ and R$_{12}$ are linear alkyl or branched alkly, they and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention when R$_{11}$ and R$_{12}$ are alkylphenyl, they may be preferably C$_1$ to C$_8$ alkylphenyl, C$_1$ to C$_4$ alkylphenyl. Some examples are methylphenyl, ethylphenyl, n- or i-propylphenyl, n-, i- or t-butylphenyl, hexylphenyl, octylphenyl, dodecylphenyl, and dimethylphenyl.

In the context of the invention when R$_{11}$ and R$_{12}$ are alkylbenzyl, they may be preferably C$_1$ to C$_8$ alkylbenzyl, C$_1$ to C$_4$ alkylpenzyl. Some examples are methylbenzyl, ethylbenzyl, n- or i-propylbenzyl, n-, i- or t-butylbenzyl, hexylbenzyl, octylbenzyl, dodecylbenzyl, and dimethylbenzyl.

In the context of the invention $R_{11}$ and $R_{12}$ independently from one another mean preferably H, $C_1$ to $C_4$ alkyl, cyclohexyl, phenyl, benzyl, $C_1$ to $C_4$ alkylphenyl or $C_1$ to $C_4$ alkylbenzyl, or $R_{11}$ and $R_{12}$ together mean tetramethylene, pentamethylene, or the group —$CH_2$—$CH_2$—O—$CH_2$—$CH_2$—.

In the context of the invention when $R_{13}$ is alkylene, it is preferably $C_1$ to $C_6$ alkylene, $C_1$ to $C_4$ alkylene, for example methylene, ethylene, propylene or butylene. Most preferred $R_{13}$ is methylene, ethylene, phenylene or benzylene.

In the context of the invention when $R_{14}$ is alkyl, it may be linear alkyl or branched alkyl and contain preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl. $R_{14}$ is preferably H, $C_1$ to $C_{12}$ alkyl, cyclopentyl, cyclohexyl, phenyl, benzyl.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-$SO_2$, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl, $CH_3$—CO—, $C_6H_5$—CO—, $CH_3$—CO—O—, $C_6H_5$—CO—O—, $CH_3$—$SO_2$—O—, $C_6H_5$—$SO_2$—O—, —$NH_2$, —$NHCH_3$, —$NHC_2H_5$, —$NHC_8H_{17}$, —$N(CH_3)_2$, —COOH, —CO—$OCH_3$, —CO—$OC_2H_5$, $SO_3H$, —$SO_2$—$OCH_3$, $SO_2$—$OC_2H_5$, —CO—$NH_2$, —CO—$NCH_3$, —CO—$NHC_2H_5$, —CO—$NHC_8H_{17}$, —CO—$NH(CH_3)_2$, —$SO_2$—$NH_2$, —$SO_2$—$NHCH_3$, —$SO_2$—$NHC_2H_5$, —$SO_2$—$NHC_8H_{17}$, —$SO_2$—$N(CH_3)_2$, $H_2N$—$SO_2$—, methoxymethyl, methoxyethyl, ethoxyethyl, —$(OCH_2CH_2)_2$—OH, —CN and —$NO_2$.

The number of substituents usually is arbitrary and depends essentially upon synthetic possibilities, the desired optical properties related to fluorescence and absorption, and the desired solubility.

In a preferred embodiment of the invention the compounds of formula VI correspond to formula VII,

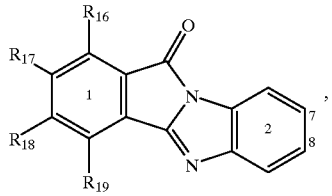

(VII)

wherein
$R_{16}$, $R_{17}$, $R_{18}$ and $R_{19}$ are independently from one another H, $C_1$ to $C_{18}$ alkyl, $C_1$ to $C_{18}$ alkoxy,
$C_1$ to $C_{18}$ alkylthio, aryl, aralkyl, $C_1$ to $C_{12}$ alkyl-aryl or $C_1$ to $C_{12}$ alkyl-aralkyl, and
the ring 2 is unsubstituted or substituted as described before, including the preferred substituents.

$C_4$ alkylphenyl. Some examples are methylphenyl, ethylphenyl, n- or i-propylphenyl, n-, i- or t-butylphenyl, hexyiphenyl, octylphenyl, dodecylphenyl, and dimethylphenyl.

In the context of the invention $R_{16}$, $R_{17}$, $R_{18}$ and $R_{19}$ in the meaning of alkyl-aralkyl may be preferably alkyl-benzyl, more preferably $C_1$ to $C_8$ alkylbenzyl, and most preferably $C_1$ to $C_4$ alkylbenzyl. Some examples are methylbenzyl, ethylbenzyl, n- or i-propylbenzyl, n-, i- or t-butylbenzyl, hexylbenzyl, octylbenzyl, dodecylbenzyl, and dimethylbenzyl.

In a particularly preferred embodiment of the invention the ring 2 is also substituted, particularly in the 7-position, in the 8-position or in both with in organic group substituent.

In a particularly preferred embodiment of the invention the compounds of formula VII corresponds to formula VIII,

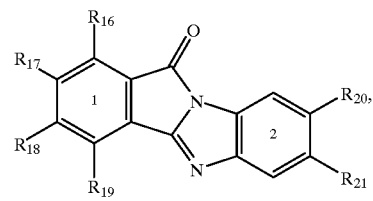

(VIII)

wherein
$R_{16}$, $R_{17}$, $R_{18}$ and $R_{19}$ are phenyl or $C_1$ to $C_{12}$ alkylphenyl,
$R_{20}$ is H or an organic group substituent, and
$R_{21}$ is H or an organic group substituent, or
the ring 2 is substituted by 1 or 2 groups selected from —CH=CH—CH=CH—.

The ring 2 is preferably monosubstituted, meaning that one of $R_{20}$ and $R_{21}$ is an organic group substituent.

$R_{16}$, $R_{17}$, $R_{18}$ and $R_{19}$ are particularly preferred phenyl.

In the context of the invention $R_{20}$ or $R_{12}$ in the meaning of an organic group substituent are preferably selected from the group consisting of —CN, —$NO_2$, $C_1$ to $C_{18}$ alkyl, $C_2$ to $C_{18}$ alkenyl, $C_2$ to $C_{18}$ alkynyl, $C_1$ to $C_{18}$ hydroxyalkyl, $C_1$ to $C_{18}$ halogenalkyl, $C_3$ to $C_{12}$ cycloalkyl, $C_6$ to $C_{18}$.

Preferably at least one of $R_{16}$, $R_{17}$, $R_{18}$ and $R_{19}$ is one of the defined substituents. More preferably $R_{17}$ and $R_{18}$ are one of the defined substituents. Mostly preferred $R_{16}$, $R_{17}$, $R_{18}$ and $R_{19}$ are substituents.

In the context of the invention $R_{16}$, $R_{17}$, $R_{18}$ and $R_{19}$ may be in the meaning of alkyl linear or branched and contains preferably 1 to 12 C-atoms, more preferably 1 to 8 C-atoms, most preferably 1 to 6 C-atoms and particularly preferred 1 to 4 C-atoms. Some examples are methyl, ethyl, n- or i-propyl, n-, i- or t-butyl, and the isomers of pentyl, hexyl, heptyl, octyl, nonyl, decyl, undecyl, dodecyl, tridecyl, tetradecyl, pentadecyl, hexadecyl, heptadecyl and octadecyl.

In the context of the invention $R_{16}$, $R_{17}$, $R_{18}$ and $R_{19}$ may be in the meaning of alkoxy linear or branched and contains preferably 1 to 12 C-atoms, more preferably 1 to 8 C-atoms, most preferably 1 to 6 C-atoms and particularly preferred 1 to 4 C-atoms. Some examples are methoxy, ethoxy, n- or i-propoxy, n-, i- or t-butoxy, and the isomers of pentoxy, hexoxy, heptoxy, octoxy, nonyloxy, decyloxy, undecyloxy, dodecyloxy, tridecyloxy, tetradecyloxy, pentadecyloxy, hexadecyloxy, heptadecyloxy and octadecyloxy.

In the context of the invention $R_{16}$, $R_{17}$, $R_{18}$ and $R_{19}$ may be in the meaning of alkylthio linear or branched and contains preferably 1 to 12 C-atoms, more preferably 1 to 8 C-atoms, most preferably 1 to 6 C-atoms and particularly preferred 1 to 4 C-atoms. Some examples are methylthio, ethylthio, n- or i-propylthio, n-, i- or t-butylthio, and the isomers of pentylthio, hexylthio, heptylthio, octylthio, nonylthio, decylthio, undecylthio, dodecylthio, tridecylthio, tetradecylthio, pentadecylthio, hexadecylthio, heptadecylthio and octadecylthio.

In the context of the invention $R_{16}$, $R_{17}$, $R_{18}$ and $R_{19}$ may be in the meaning of aryl naphthyl or preferably phenyl.

In the context of the invention $R_{16}$, $R_{17}$, $R_{18}$ and $R_{19}$ may be in the meaning of aralkyl preferably arylmethyl or -ethyl, and aryl means preferably phenyl or naphthyl. Some examples are benzyl, phenylethyl and naphthylmethyl.

In the context of the invention $R_{16}$, $R_{17}$, $R_{18}$ and $R_{19}$ may be in the meaning of alkyl-aryl preferably alkylphenyl, more preferably $C_1$ to $C_8$ alkylphenyl, and most preferably $C_1$ to aryl, $C_3$ to $C_{12}$ cycloalkyl-alkyl, $C_6$ to $C_{18}$ aralkyl, $C_1$ to $C_{18}$ alkyloxy, $C_3$ to $C_{12}$ cycloalkyloxy, $C_6$ to $C_{18}$ aryloxy, $C_3$ to $C_{12}$ cycloalkyl-alkyloxy, $C_6$ to $C_{18}$ aralkyloxy, $C_1$ to $C_{18}$ alkylthio, $C_3$ to $C_{12}$ cycloalkylthio, $C_6$ to $C_{18}$ arylthio, $C_3$ to $C_{12}$ cycloalkyl-alkylthio, $C_6$ to $C_{18}$ aralkylthio, $C_1$ to $C_{18}$ alkyl-CO—, $C_3$ to $C_{12}$ cycloalkyl-CO—, $C_6$ to $C_{18}$ aryl-CO—, $C_3$ to $C_{12}$ cycloalkylalkyl-CO—, $C_6$ to $C_{18}$ aralkyl-CO—, —$NR_{11}R_{12}$, alkoxyalkyl with 2 to 20 carbon atoms, polyoxyalkylene-$OR_{14}$, —X—$(R_{13})_k$—C(O)—$NR_{11}R_{12}$, —X—$(R_{13})_k$—C(O)—$OR_{14}$, —X—$(R_{13})_k$—$SO_{2OR14}$, —X—$(R_{13})_k$—$SO_2$—$NR_{11}R_{12}$, —NH—C(O)—$R_{14}$ and —O—C(O)—$R_{14}$, wherein $R_{11}$ and $R_{12}$ independently from one another mean H, $C_1$ to $C_{20}$ alkyl, cyclopentyl, cyclohexyl, phenyl, benzyl, $C_1$ to $C_{12}$ alkylphenyl or $C_1$ to $C_{12}$ alkylbenzyl, or $R_{11}$ and $R_{12}$ together mean tetramethylene, pentamethylene, or the groups —$CH_2$—$CH_2$—O—$CH_2$—$CH_2$— or —$CH_2$—$CH_2$—$NR_{15}$—$CH_2$—$CH_2$—, $R_{13}$ is $C_1$ to $C_{12}$ alkylene, phenylene or benzylene, $R_{14}$ means H, $C_1$ to $C_{20}$ alkyl, cyclopentyl, cyclohexyl, phenyl, benzyl, $C_1$ to $C_{12}$ alkylphenyl or $C_1$ to $C_{12}$ alkylbenzyl, $R_{15}$ is H or $C_1$ to $C_4$ alkyl, X is a direct bond, —O— or S, k is 0 or 1 and and the salts of the acids.

The preferred meanings described before are also valid for the meanings of $R_{20}$, $R_{21}$, X and $R_{11}$ to $R_{14}$.

$R_{20}$ and $R_{21}$ in the meaning of an organic group substituent are most preferably selected from the group consisting of —CN, —$NO_2$, $C_1$ to $C_{18}$ alkyl, $C_1$ to $C_{18}$ hydroxyalkyl, $C_5$ to $C_7$ cycloalkyl, $C_6$ to $C_{10}$ aryl, $C_7$ to $C_{11}$ aralkyl, $C_1$ to $C_{18}$ alkyloxy, $C_3$ to $C_{12}$ cycloalkyloxy, $C_6$ to $C_{10}$ aryloxy, $C_5$ to $C_7$ cycloalkyl-alkyloxy, $C_7$ to $C_{11}$ aralkyloxy, $C_1$ to $C_{18}$ alkylthio, $C_5$ to $C_7$ cycloalkylthio, $C_6$ to $C_{10}$ arylthio, $C_5$ to $C_7$ cycloalkyl-alkylthio, $C_7$ to $C_{11}$ aralkylthio, $C_1$ to $C_{18}$ alkyl-CO—, $C_5$ to $C_7$ cycloalkyl-CO—, $C_6$ to $C_{10}$ aryl-CO—, $C_5$ to $C_7$ cycloalkyl-alkyl-CO—, $C_7$ to $C_{11}$ aralkyl-CO—, —$NR_{11}R_{12}$, alkoxyalkyl with 2 to 12 carbon atoms, polyoxyalkylene-$OR_{14}$, —X—$(R_{13})_k$—C(O)—$NR_{11}R_{12}$, —X—$(R_{13})_k$—C(O)—$OR_{14}$, —X—$(R_{13})_k$—$SO_2$—$OR_{14}$, —X—$(R_{13})_k$—$SO_2$—$NR_{11}R_{12}$, —NH—C(O)—$R_{14}$ and —O—C(O)—$R_{14}$, wherein $R_{11}$ and $R_{12}$ independently from one another mean H, $C_1$ to $C_6$ alkyl, cyclopentyl, cyclohexyl, phenyl, benzyl, $C_1$ to $C_6$ alkylphenyl or $C_1$ to $C_6$ alkylbenzyl, or $R_{11}$ and $R_{12}$ together mean tetramethylene, pentamethylene, or the group —$CH_2$—$CH_2$—O—$CH_2$—$CH_2$—, $R_{13}$ is $C_1$ to $C_4$ alkylene, phenylene or benzylene, $R_{14}$ means H, $C_1$ to $C_{12}$ alkyl, cyclopentyl, cyclohexyl, phenyl, benzyl, $C_1$ to $C_6$ alkylphenyl or $C_1$ to $C_6$ alkylbenzyl, X is a direct bond, —O— or S, k is 0 or 1 and and the salts of the acids.

In a particularly preferred embodiment of the invention $R_{20}$ and $R_{21}$ are selected from the group consisting of —$NO_2$, $C_1$ to $C_{18}$ alkyl, which is linear or branched, $C_1$ to $C_{18}$ alkyloxy, which is linear or branched, —C(O)OH, or —C(O)—O—$C_1$ to $C_{18}$ alkyl.

The compounds of formulae I and Ia are partially known or can be easily prepared from unsubstituted or substituted orthophenylenediamines and from unsubstituted or substituted phthalic anhydride as described for example in EP-A-0 456 609.

Polymers which may be used as a polymer matrix may be selected from the group consisting of thermoplastics, polymer blends, thermosettings and structurally crosslinked polymers. The polymers may be homopolymers, copolymers, blockpolymers, graft polymers, emulsion polymers or random polymers.

The polymers may be opaque, translucent or transparent, preferably transparent. The polymers may be selected for example from the group of thermoplastic polymers like polyesters, polyamides, polyimides, polyamide-imides, polyamide esters, polyurethanes, polyureas, polyolefines; polymers from substituted olefines like vinylethers, vinylesters, vinylalcohols, vinylchloride, vinyldichloride, acrylonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone; polymaleic acid and esters and amides therefrom; polyethers (for example from bisphenol-A diglycidyl ether), polysulfones, polyketones, polyphenylsulfides, and polyacetales; and natural polymers and their derivatives like cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenol/formaldehyde resins; polymers from butadiene, isoprene and or chloroprene and copolymers with olefins, which may be crosslinked and rubbery in nature, including latices; as well as silicates obtainable for example through the known sol/gel process.

The polymeric compositions of the invention may contain further ingredients to enhance certain features such as electrical, physical and mechanical properties, and/or the processability, for example dispersing agents to achieve a uniform distribution of particles, lubricants, plasticizers, antistatica, solvents, molding agents, antioxidants, light stabilizers, fillers and reinforcing fillers like glass beads and glass fibbers, quartz powder, silicates (e.g. mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

The total amount of dissolved pigment, or pigment precursor, in the polymer matrix, in the absence of host chromophore, may be for example from 0.001 to 10 weight %, preferably 0.1 to 10 weight %, more preferably 1 to 8 weight %, and most preferably 1 to 5 weight %, related to the total composition, will furnish highly fluorescent materials. The total amount of dissolved pigment, or pigment precursor, in the polymer matrix, in the presence of a host chromophore, may be for example from 0.001 to 10 weight %, preferably 0.01 to 8 weight %, more preferably 0.01 to 5 weight %, and most preferably 0.01 to 3 weight %, related to the total composition.

In applications where a host and a pigment or a pigment precursor are dissolved in a polymer matrix, the amount of host chromophores is dependent on the actual practical application, hence there are no well defined preferred ratios, other than the broad range 90:10 to 1:999 (host/pigment or pigment precursor, resp.). In certain applications where both color strength and fluorescence are required, then the preferred weight ratio of host to pigment, or pigment precursor, resp., is usually in the range of from 10 to 90 wt %, preferably from 20 to 90 wt % and more preferably from 50 to 90 wt %. In circumstances where fluorescence is desired, but color strength is not required, then the weight ratio of host to pigment or pigment precursor, resp., may be chosen in the range of from 0.01 to 50 wt %, more preferably from 0.01 to 20 wt % and more preferably from 0.01 to 10 wt %.

Another preferred embodiment of the present invention relates to a composition comprising a polymer matrix or a polymer precursor, and/or a host chromophore, and a pigment precursor, wherein in all cases where there is a host component, the absorption spectrum of the pigment (as guest chromophore), obtainable from the pigment precursor, overlaps with the fluorescence emission spectrum of the host chromophore.

Another preferred embodiment of the present invention relates to a composition comprising a polymer matrix or a polymer precursor, and/or a host chromophore, and a pigment, wherein in all cases where there is a host component, the absorption spectrum of the pigment (guest chromophore) overlaps with the fluorescence emission spectrum of the host chromophore.

Another preferred embodiment of the present invention concerns a composition obtainable by (1) mixing a host chromophore and an effective amount of a pigment precursor in a solvent, then generating a pigment as guest chromophore in-situ from the pigment precursor, and, subsequently, isolating the mixture of the host and guest chromophores thereby forming a solid solution, or (2) mixing a polymer as a matrix or a polymer precursor and a pigment precursor in a solvent, if desired in the presence of a chromophore being a host component, then generating a pigment in-situ from the pigment precursor (being the guest component if a host component is present), and, subsequently, isolating the mixture of polymer and pigment, and—if present—the host component, thereby forming a solid solution, wherein in all cases where there is a host component, the absorption spectrum of the pigment (guest chromophore) overlaps with the fluorescence emission spectrum of the host chromophore.

It was found that inherently insoluble pigments can be molecularly incorporated into a polymer matrix, in a ready manner, to generate highly fluorescent polymeric materials. It was also found that these materials in general show an enhanced emission fluorescence and a large shift between the respective excitation spectra and the emission spectra of the system, which might be due to the occurrence of resonant energy transfer, when a host chromophore is additionally incorporated; or alternatively, when the pigment functions as host chromophore, a guest chromophore is additionally incorporated.

A further preferred embodiment of the present invention relates to a solid composition comprising (1) a host chromophore and distributed, preferably homogeneously, therein a pigment precursor, wherein the amount of pigment precursor usually is at most 10 weight percent of the total composition; or (2) a polymer matrix and distributed, preferably homogeneously, therein a pigment precursor and a host chromophore, wherein the amount of pigment precursor in general is at most 10 weight percent of the total composition, and wherein the absorption spectra of the pigment precursor overlaps with the fluorescence emission spectrum of the host chromophore.

In a more preferred embodiment thereof, the pigment precursor is, in addition, dissolved, preferably molecularly, either in a matrix formed by the host chromophore, or the pigment precursor and the host chromophore are dissolved, preferably molecularly, in the matrix formed by the polymer.

All the embodiments and preferences described above are also valid for this composition.

Another preferred embodiment of the present invention is a process for the preparation of a powder characterized in mixing a pigment or a pigment precursor, a chromophore H and a solvent, preferably homogeneously, precipitating the pigment or pigment precursor together with the chromophore H thereby obtaining a precipitate, then separating the precipitate, if desired, washing the separated precipitate, and drying it.

In a more preferred embodiment the chromophore H is a host chromophore, for example, selected from the host chromophores mentioned already above, and the pigment or pigment precursor acts as a guest chromophore, wherein the absorption spectra of the pigment precursor overlaps with the fluorescence emission spectrum of the host chromophore.

In another more preferred embodiment of the abovementioned process, the separated precipitate containing the pigment precursor is heat-treated, thereby generating a pigment in-situ.

A still further preferred embodiment of the present invention relates to a powder obtained by the abovementioned processes, preferably containing particles.

Another preferred embodiment of the present invention relates to a process for the preparation of a layer on a solid support material characterized in heating a composition consisting essentially of a chromophore H and a pigment precursor or a pigment, preferably the inventive powder described above, in the presence of a solid support material, and depositing the chromophore H together with the originally pigment or the pigment obtained in-situ during this process from the pigment precursor on the solid support material, wherein the absorption spectrum of the pigment overlaps with the fluorescence emission spectrum of the chromophore H.

Another preferred embodiment of the present invention relates to a solid composition in the form of particles, which comprises a host chromophore matrix and, if desired dissolved, and, preferably homogeneously, distributed therein a pigment precursor or a pigment, wherein the amount of pigment precursor, or pigment, preferably is at most 10 weight percent of the total composition, and wherein the absorption spectrum of the pigment precursor, or the pigment, overlaps with the fluorescence emission spectrum of the host chromophore.

Another preferred embodiment of the present invention relates to a powder consisting essentially of polymer particles containing the abovementioned pigment precursor or pigment and optionally host chromophores, if desired dissolved and, distributed therein, preferably homogeneously, which in general is obtainable through grinding or emulsion polymerization, aqueous suspension polymerization or a combination thereof.

The particles of the powder may have an average diameter in the range from 10 nm to 500 $\mu$m, more preferably from 50 nm to 100 $\mu$m, and most preferably from 50 nm to 50 $\mu$m.

Another object of the invention is a carrier material, wherein at least one surface of it is coated with a layer of a composition comprising (1) a host chromophore matrix and distributed therein, preferably homogeneously, a pigment precursor, wherein the amount of pigment precursor preferably is at most 10 weight percent of the total composition, or (2) a polymer matrix, and therein distributed, preferably homogeneously, a pigment precursor and a host chromophore, wherein the amount of pigment precursor preferably is at most 10 weight percent of the total composition, and wherein the absorption spectra of the pigment precursor overlap with the fluorescence emission spectrum of the host chromophore.

In a more preferred embodiment of the abovementioned carrier material, the pigment precursor is dissolved, preferably molecularly, within the host chromophore matrix (variant 1), or the pigment precursor and the host chromophore are dissolved, preferably molecularly, within the polymer matrix (variant 2).

Suitable carrier materials may be selected from organic or inorganic materials such as glass, ceramics, minerals, plastics, paper, wood, semiconductors, metals, metal oxides and semiconductor metal oxides, and metal or semiconductor metalnitrides or -carbides.

Usually, the thickness of the layer depends on the desired use and may be in the range from 0.01 to 1000 $\mu$m, preferably from 0.05 to 500 $\mu$m, and particularly preferred from 0.1 to 100 $\mu$m.

In a still further preferred embodiment the coatings may be protected by cover layers which are preferably transparent. Such coatings are well known and in general, photocrosslinked coatings are mainly used for this purpose, and are well known in the art. Preferred coatings are transparent.

Preferably the inventive pigment precursor containing compositions can all be used to generate a fluorescent pigment, which is distributed, preferably homogeneously, in a polymer matrix, and more preferred homogeneously distributed and molecularly dissolved in the matrix.

A further preferred embodiment of the present invention is a composition comprising a polymer matrix, and distributed, preferably homogeneously, therein a fluorescent pigment. More preferred is a composition, wherein the fluorescent pigment is molecularly dissolved and homogeneously distributed within the polymer matrix.

The amount of pigments is described above, incorporated by reference.

The former disclosed embodiments and preferences are also valid for this composition.

In an preferred embodiment the composition additionally contains a soluble host chromophore, for example the afore mentioned host chromophores, including the preferences. In case the emission spectrum of the dissolved host chromophores overlaps with the absorption spectrum of the fluorescent dissolved pigment, the dissolved pigment functions as a guest chromophore, which preferably affords an enhanced fluorescence.

Host and guest chromophores for this application have been mentioned previously.

Solid solutions of a pigment precursor in a host chromophore may be used, where the pigment preferably is deliberated by thermal treatment to generate the powders. It is also possible that the composition containing the molecularly dissolved pigment, in the host matrix, can be simply ground into powders.

Another preferred embodiment of the present invention relates to a composition containing a pigment, preferably dissolved, more preferred molecularly dissolved, in a host matrix, preferably in the form of powders, which can be sublimed together at the same time from one single container and deposited as a layer on a carrier material, whereby the layer still contains the pigment, preferably in a dissolved state, most preferred in a molecularly dissolved state.

Another preferred embodiment of the present invention relates to a process for the preparation of a layer on a solid support (or carrier) material wherein the layer composition is comprised of a matrix formed by a host chromophore and distributed therein, preferably homogeneously, more preferred dissolved and homogeneously distributed therein, a fluorescent pigment, wherein the amount of pigment preferably is at most 10 weight percent of the layer composition, and wherein the absorption spectrum of the pigment overlaps with the fluorescence emission spectrum of the host chromophore, whereby a powder of a composition, containing the host chromophore matrix and a fluorescent pigment, or a pigment precursor, distributed therein, preferably homogeneously, more preferred molecularly dissolved and homogeneously distributed therein, is heated ("sublimed"), preferably in an atmosphere with a reduced pressure, and deposited on at least one surface of the support material.

If a pigment precursor is used, in general the temperature depends on the choice of the pigment precursor. Usually, the temperature is chosen preferably in the range of from 50 to 250° C., more preferably from 80 to 200° C., and most preferably from 100 to 180° C. The pressure usually is chosen not higher than 100 kPa, preferably the pressure is not higher than $1\times10^{-2}$ Torr, more preferably not higher than $1\times10^{-3}$ Torr, most preferably not higher than $1\times10^{-4}$ Torr.

The compositions according to the invention may be milled to generate a powder form, which can be very convenient for many industrial applications.

The particles of the composition of the invention also may be encapsulated with polymers by known methods to generate for example another form of pigments for coloring polymers.

The compositions according to the invention may be coated as layer(s) on support materials, obtainable through well known coating processes. Hence, a further preferred embodiment of the present invention relates to a support material, to which on at least one surface a layer of the polymer composition according to the invention is coated.

Suitable carrier materials may be selected from organic or inorganic materials like glass, ceramics, minerals, plastics, paper, wood, semiconductors, metals, metal oxides and semicon ductor metal oxides, and metal or semiconductor metalnitrides or -carbides.

The thickness of the layer usually depends on the desired use and preferably may be in the range from 0.01 to 1000 $\mu$m, preferably ffrom 0.05 to 500 $\mu$m, and particularly preferred from 0.1 to 100 $\mu$m.

The coatings may be protected by cover layers which preferably are transparent. Such coatings are well known and in general photocrosslinked coatings are mainly used for this purpose, and are well known in the art. Preferred coatings are transparent.

The powders, containing particles, of the polymer compositions according to the invention may be admixed with polymers. A further preferred embodiment of the present invention relates to a composition comprising (a) a polymer substrate, and (b) particles of the polymer composition according to the invention or particles of a composition containing a host chromophore matrix and a pigment, preferably molecularly dissolved, or both, homogeneously distributed therein.

The amount of particles in general is dependent on the actual practical application, hence there are no well defined preferred ratios, other than the broad range 90:10 to 1:999 (particles:polymer). In certain applications where both color strength and fluorescence are required, then the preferred weight ratio of particles to polymer is from 10 to 90 wt %, preferably from 20 to 90 wt %, and more preferably from 50 to 90 wt %. In circumstances where fluorescence is desired but color strength is not required, then the weight ratio of particles preferably is in the range of from 0.01 to 50 wt %, more preferably from 0.01 to 20 wt %, and more preferably from 0.01 to 10 wt %.

The polymer substrate may be selected from thermoplastics, polymer blends, thermosettings and structurally crosslinked polymers. The polymers may be homopolymers, copolymers, blockpolymers, graft polymers, alternating copolymers or random polymers.

The polymers may be opaque, transparent or translucent, preferably transparent. The polymers may be selected for example from the group consisting of thermoplastic polymers like polyesters, polyamides, polyimides, polyamide-imides, polyamide esters, polyurethanes, polyureas, polyolefines; polymers from substituted olefines like vinylethers, vinylesters, vinylalcohols, vinylchloride, vinyldichloride, acetonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone: polymaleic acid and esters and amides therefrom; polyethers (for example from bisphenol-A diglycidyl ether), polysufones, polyketones, polyphenylsulfides, and polyacetales; and natural polymers and their derivatives like cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenol/formaldehyde resins; polymers from butadiene, isoprene and or chloroprene and copolymers with olefins, which may be crosslinked and of rubbery nature; as well as silicates obtainable for example through the known sol/gel process.

The thermoplastic compositions in general are obtainable by well known mixing methods, such as admixing solutions of polymers and removing the solvent, injection molding and extrusion molding. Thermosetting and structurally crosslinked compositions usually are obtainable by known methods like press molding, whereby the particles preferably are dispersed prior to the polymerization of a precursor composition.

The polymeric compositions of the invention may contain further ingredients to enhance certain properties such as electrical, physical and mechanical properties, and/or the processability, for example dispersing agents to achieve a uniform distribution of particles, lubricants, plasticizers, antistatica, solvents, molding agents, antioxidants, light stabilizers, fillers and reinforcing fillers like glass balls and glass fibbers, quartz powders, silicates (e.g. mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

The polymer compositions of the invention preferably may be used in the form of shaped articles.

The polymer compositions or polymerisable precursor compositions with particles preferably may contain a solvent to generate coating compositions. Suitable solvents have been mentioned previously.

In another aspect of the invention the polymer composition containing polymer may be used as coatings on carrier materials, using the aforementioned composition.

Another preferred embodiment of the invention relates to a composition comprising (a) a carrier material and (b) at least on one surface a coating of a composition comprising (c) a polymer matrix, and (d) polymer particles of the composition according to the invention, or particles of a composition containing a host chromophore matrix and a pigment, preferably molecularly dissolved, or both, distributed therein, preferably homogeneously.

The coatings preferably may be protected by overlays which are preferably transparent. Such coatings in general are well known and preferably photocrosslinked coatings are mainly used for this purpose.

The coated materials usually are obtainable by known methods like painting, casting or spincoating, directly or with dispersion of the polymeric compositions.

It is also possible to use a polymerisable composition containing polymer forming monomers or oligomeric precursors, particularly crosslinkable olefinically unsaturated monomers, to generate coatings. The polymerization may be induced thermally or by actinic radiation or both. The preparation of this composition preferably can be achieved by simply mixing the ingredients together using suitable mixing equipment. Dispersions are in general stable depending upon the viscosity. If particles should aggregate they may be redistributed by stirring. In a highly advantageous embodiment of preparing coatings polymerisable compositions can be used, wherein at least one surface of a carrier material is coated and subsequently polymerized by heat, radiation or both. Photopolymerizable mixtures can also be used to generate fluorescent images by known photoresist technology.

The composition may be used to generate the polymers or polymer particles according to the invention as described before. Preferably the composition contains a solvent, when coatings or images are to be generated. The afore described embodiments also apply to this composition, including the preferred embodiments.

In another preferred embodiment the composition is based on polymerisable monomers and/or prepolymers containing a functional group selected from olefinically unsaturated groups, preferably from —CH=CH$_2$ and —C(CH$_3$)=CH$_2$, which can be thermally polymerized or photopolymerized.

Photopolymerisable monomers and prepolymers are well known in the art and described for example in EP-A-0 654 711. Preferred photopolymerisable monomers and prepolymers are those based on the esters or amides of acrylic acid or methacrylic acid and alcohols, polyols, amines and polyamines.

Preferred ethylenically unsaturated photopolymerisable agents are selected from the group of acrylic or methacrylic acid esters of aliphatic, cycloaliphatic and cycloaliphatic-aliphatic alcohols and diols to tetrols, and amines and diamines to tetramines containing particularly preferred 2 to 12, and particularly preferred 2 to 8 C-atoms. Some examples of these diols are alkylenediols like ethylenglycol, 1,2- or 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxyalkylendiols from preferably C$_2$–C$_6$alkylendiols with preferably 2 to 100 alkylenediol units, more preferably 2 to 50 alkylenediol units, and most preferably 2 to 20 alkylenediol units, like for example polyethylenediols, polypolypropylenediols, polybutylenediols and polyethylene/polypropylenediols, further 1,1,1- trihydroxymethylethane or -propane, pentaerythritol and dipentaerythritol. Some examples for polyamines are ethylenediamine, 1,3- and 1,3-propanediamine, 1,2-, 1,3- and 1,4-butanediamine, 1,6-hexanediamine, diethylenetriamine, triethylenetetramine, cyclohexanediamine, (aminomethyl)cyclohexaneamine, isophorondiamine and di(aminomethyl)cyclohexane. Examples of alcohols are linear or branched $C_1$ to $C_{20}$ alkanols.

The photopolymerisable composition is particularly suitable for generating coatings and images.

A further preferred embodiment of the present invention relates to a composition comprising (a) a carrier material and on at least one surface of the carrier is coated (b) a high relief image of a polymerized photoresist material, which contains particles of the polymer composition according to the invention or particles composed of a host matrix and a pigment, preferably molecularly dissolved, or both, distributed therein, preferably homogeneously.

Another preferred embodiment of the present invention relates to a process for the creation of fluorescent radiation which requires the excitation either electrically or by UV or visible radiation, or both, of a fluorescent composition according to the invention.

Another preferred embodiment of the present invention relates to the use of the compositions according to the invention as fluorescent materials.

The fluorescent composition of the present invention emits solid state fluorescence with a greatly enhanced emission intensity when compared to the solid-state emission intensity of a composition that contains host units but lacks any guest units, or a composition that contains guest units but lacks any host units.

All the materials described before preferably may be used in optical and electrooptical devices.

The compositions on hand do show the following advantages compared to known compositions:

a) a highly uniform distribution of inherently insoluble pigment in a host chromophore or in a polymer matrix can be achieved;

b) a solid solution can be achieved, wherein an insoluble pigment is dissolved in a molecularly state and thus homogeneously distributed in a host chromophore;

c) fluorescent materials are generated from polymers as matrix and contain a dissolved pigment;

d) fluorescent materials with enhanced luminescence are obtained by the co-use of a host chromophore and energy transfer from the host to the pigment even in a polymer matrix;

e) the manufacturing process is far less expensive than the known co-sublimation technique;

f) high amounts can be produced within short periods of time; and g) an economic industrial scale production can be achieved;

h) even an easy preparation of fluorescent particles comprising a host chromophore matrix and a pigment can be achieved;

i) fluorescent layers of a host chromophore matrix and a pigment can be directly achieved from the powder form host chromophore/pigment mixtures;

j) fluorescent layers of a host chromophore matrix and a pigment can be even directly achieved from the powder form host chromophore/pigment precursor mixtures; when the insoluble pigmentary guest chromophore is incorporated into the host chromophore or in a polymer matrix with or without a dissolved host chromophore using a soluble and decomposable pigment precursor, limiting the upper content of the pigment in the matrices, and the decomposition conditions must be controlled to avoid unwanted migration of the deliberated pigment.

Further, a preparation method was found which is much more simple and convenient as the methods of the conventional art using separate sources of host and guest for sublimation as described for example in U.S. Pat. No. 5,227,252 and JP-A-05 320 633. The co-sublimation of a simple mechanical mixture of the host and pure pigment (i.e. not precursor) components from one a single container does not result in generating materials of this invention.

Another preferred embodiment of the present invention relates to the use of the solid fluorescent compositions prepared according to the inventive process as organic emitting materials in and for the preparation of electroluminescence ("EL") devices. Those EL-devices are well known in the art and e.g. described in U.S. Pat. No. 5,593,788, WO 94/15441, and the literature cited therein. For example one of the common EL devices comprises two extremely thin layers (<1.0 μm in combined thickness) which separate the anode and the cathode. One layer specifically is chosen to inject and transport holes and the other specifically chosen to inject and transport electrons and also acting as the organic luminescent zone of the device. The extremely thin organic luminescent medium offers reduced resistance, permitting higher current densities for a given level of electrical biasing. Since light emission is directly related to current density through the organic luminescent medium, the thin layers coupled with increased charge injection and transport efficiencies have allowed acceptable light emission levels (e.g. brightness levels capable of being visually detected in ambient light) to be achieved with low voltages in ranges compatible with integrated circuit drivers, such as transporting layer also acting as the luminescent zone of the device.

In another preferred embodiment of this invention, the inventive host/guest solid solutions, either with or without a polymer, and the inventive compositions comprising a polymer, a host chromophore and either a pigment precursor or a pigment (obtainable from the pigment precursor) can be used as organic emitting material in a layer of an EL device as well as for the preparation of such an EL device. Such devices are known in principle e.g. from U.S. Pat. No. 5,593,788 and the prior art cited therein, hence, no further details are necessary for a skilled person in the art.

Hence, electroluminescent devices comprising an anode, a cathode and as organic emitting material the inventive solid solutions or compositions are also part of this invention. The preparation of such devices is given in detail e.g. in the above cited U.S. Pat. No. 5,593,788 or WO 94/15441.

In a particularly preferred embodiment, a EL device comprises an anode, e.g. an ITO glass substrate, a cathode, e.g. magnesium, a hole-transporting substance, e.g. TPD (N,N'-diphenyl-N,N'-bis(3-methylphenyl)-1,1'-biphenyl-4,4'-diamine, and a light-emitting material, preferred a pigment or pig,ent precursor as described above, particularly preferred a pigment precursor such as one of the abovementioned DPP-BOC compounds.

In another preferred embodiment of this invention, the light-emitting material and, optionally a hole-transporting material, are deposited on one of the electrodes, either cathode or anode, by sublimation, particularly preferred the light-emitting layer is obtained by the simultaneous sublimation of a host chromophore and a guest chromophore, wherein the abovementioned definitions for the host and guest compounds are valid, preferred is the sublimation of an inventive host/guest mixture, particularly preferred the above described inventive powder. Hence, an electroluminescent element comprising an anode and a cathode as electrodes, and an organic light-emitting material, wherein a thin layer on one of the electrodes is obtained by sublimation of the organic light-emitting material, and wherein the organic light-emitting material is either a pigment or a pigment precursor, is also part of this invention.

A further embodiment of this invention relates to layers comprising a host and a guest, obtained by sublimation of the corresponding host/guest mixtures, wherein the host and guest compounds are as defined above, e.g. the host exhibiting a solid-state fluorescence, and a guest being a pigment or a pigment precursor, and wherein the absorption spectrum of the pigment or pigment precursor overlaps with the fluorescence emission spectrum of the host compound.

Accordingly, a further embodiment of this invention relates to a process for the preparation of a layer comprising a host and a guest compound, wherein the corresponding host/guest mixture is subjected to sublimation thereby forming a layer, wherein the host and guest compounds are as defined above, e.g. the host exhibiting a solid-state fluorescence, and a guest being a pigment or a pigment precursor, and wherein the absorption spectrum of the pigment or pigment precursor overlaps with the fluorescence emission spectrum of the host compound.

Further, an electroluminescent element comprising a cathode, an anode and a layer obtained by sublimation of the inventive host/guest mixtures.

The compositions according to the invention can span a broad number of applications as they readily facilitate themselves to excitation by both UV and daylight radiation sources. Preferably, these materials could be rendered very useful as coloring agents in applications such as road markings and traffic signs for night and daylight uses, as they exhibit brilliant daylight fluorescence and can also be excited by the UV radiation of motor vehicles halogen lamps, thereby providing intense, bright colors during both day and nighttime. Other applications include their use as pigments, coloring agents, materials for scintillators, materials for solar energy collectors, materials for light emitting electroluminescent devices, materials for generating fluorescent images. Moreover, the choice of host and guest compounds can lend a lot of flexibility to the desired emission wavelength required of the overall system, therein imparting the capability for color-tuning and ease of tailoring of the core system to specific color applications via wavelength modulation. It is also possible to produce fluorescent images (high relief structures) by the well known photoresist technology. The compositions of the invention may also be used in paintings and lacquers as well as in printing inks.

The following examples demonstrate the invention.

In the examples, the following abbreviations are used:
DPP: 1,4-diketo-3,6-diphenyl-pyrrolo-[3,4-c]pyrrole
MeDPP: 1,4-diketo-3,6-di(4-methyl-phenyl)-pyrrolo-[3,4-c]pyrrole
tBuDPP: 1,4-diketo-3,6-di(4-tert.-butyl-phenyl)-pyrrolo-[3,4-c]pyrrole
PhDPP: 1,4-diketo-3,6-di(4-biphenyl)-pyrrolo-[3,4-c]pyrrole
ClDPP: 1,4-diketo-3,6-di(4-chloro-phenyl)-pyrrolo-[3,4-c]pyrrole
QA: quinacridone
DPP-BOC: N,N'-bis-tert.-butyloxycarbonyl-1,4-diketo-3,6-diphenyl-pyrrolo-[3,4-c]pyrrole
MeDPP-BOC: N,N'-bis-tert.-butyloxycarbonyl-1,4-diketo-3,6-di(4-methyl-phenyl)-pyrrolo-[3,4-c]pyrrole
tBuDPP-BOC: N,N'-bis-tert.-butyloxycarbonyl-1,4-diketo-3,6-di(4-tert.-butyl-phenyl)-pyrrolo-[3,4-c]pyrrole
PhDPP-BOC: N,N'-bis-tert.-butyloxycarbonyl-1,4-diketo-3,6-di(4-biphenyl)-pyrrolo-[3,4-c]pyrrole
ClDPP-BOC: N,N'-bis-tert.-butyloxycarbonyl-1,4-diketo-3,6-di(4-chloro-phenyl)-pyrrolo-[3,4-c]pyrrole
QA-BOC: N,N'-bis-tert.-butyloxycarbonyl quinacridone The Solvents used in the examples are purchased from Wako Chemical Co. Ltd. Polycarbonate resin (Z200) is purchased from Mitsubishi Gas Chemical Co., Inc. Tris(8-hydroxyquinolinate) aluminum is purchased from Dojindo Laboratories. The wire bar used in the examples (KCC rod No. 8) is purchased from RK Print-Coat Instruments. The ITO glass substrate used in the examples (ITO film thickness 200 nm, sheet resistance 10 ohm/cm$^2$) is purchased from Matsuzaki Shinku Co. The homogenizer used in the examples (Ultra-Turrax T-25) is purchased from IKA-Labortechnik. The fluorescence spectrophotometer (F-4500) used to evaluate fluorescent properties is purchased from Hitachi Co. LTD.

A) PREPARATION OF FLUORESCENT POLYMER FILMS

Example A1

0.00244 g of DPP-BOC precursor is dissolved in 5.0 ml of a 10 wt % THF solution of polycarbonate resin. Then the solution is applied to a glass substrate using a wire bar coater and dried at 40° C. for 30 minutes. The color of the film is green with green fluorescence. The sample is then heat-treated at 150° C. for 30 minutes, to furnish a yellowish green film with strong yellowish green fluorescence.

Example A2

0.00279 g of ClDPP-BOC precursor is dissolved in 5.0 ml of a 10 wt % THF solution of polycarbonate resin. Then the solution is applied to a glass substrate using a wire bar coater and dried at 60° C. for 1 hour. The color of the film is green with green fluorescence. The sample is then heat-treated at 150° C. for 2 hours, to furnish a yellowish green film with strong yellowish green fluorescence.

Example A3

0.00256 g of QA-BOC precursor is dissolved in 5.0 ml of a 10 wt % THF solution of polycarbonate resin. Then the solution is applied to a glass substrate using a wire bar coater and dried at 60° C. for 1 hour. The color of the film is green with green fluorescence. The sample is heat-treated at 150° C. for a half hour, to furnish a yellowish green film with strong yellowish green fluorescence.

Determination of Fluorescence Properties of Films

The fluorescence properties of the polymer films obtained in Examples A1 to A3 are measured using a fluorescence spectrophotometer (F-4500, Hitachi Co. LTD.). The peak absorption of the fluorophore is selected as the excitation wavelength, and for all cases it is 480 nm. The results obtained are summarized in Table 1.

TABLE 1

Fluorescence properties of polymer films

| Example | Peak wavelength (nm) | Intensity (arb. units) |
|---|---|---|
| A1 | 512 | 285 |
| A2 | 523 | 290 |
| A3 | 525 | 86 |

Example A4

Carefully measured amounts of the host compound 1,2,3,4-tetraphenyl-benzo[4,5]imidazo[2,1-a]isoindol-11-one, a precursor of a guest compound (DPP-BOC or QA-BOC) and polymethylmethacrylate are dissolved in $CHCl_3$/methanol (95/5), to yield a clear, homogeneous solution (5 wt % concentration). The mixture is then cast onto a glass substrate using a wire bar, and the solvent flashed off at room temperature, to yield a polymer film that has the visual color and spectroscopic features typical of the precursor (green with green fluorescence). This film is then is heat-treated at 120° C. for the times given in table 2, resulting in a fluorescent film with yellowish green color. The fluorescence properties of the fluorescent powders are measured using a fluorescence spectrophotometer in the standard reflection mode (F-4500, Hitachi Co. LTD.) fitted with a solid sample holder. The monochromatic excitation wavelength corresponds to the absorption maximum of the host i.e. 360 nm. The results are listed in Table 2.

TABLE 2

| Host* (weight %) | Guest (weight %) | Polymer (weight %) | Heating time (min) | Peak wavelength (nm) | Peak Intensity (arb. Units) |
|---|---|---|---|---|---|
| 20 | DPP (0.1) | 80 | 6 | 509 | 229 |
| 50 | DPP (0.1) | 50 | 1 | 510 | 370 |
| 20 | QA (0.1) | 80 | 1 | 520 | 182 |
| 20 | none | 80 | 2 | 500 | 104 |

*1,2,3,4-tetraphenyl-benzo [4,5] imidazo [2,1-a] isoindol-11-one

B) PREPARATION OF HOST AND GUEST CHROMOPHORES MIXTURES

Example B1

$1 \times 10^{-5}$ mol (0.0056 g) of CIDPP-BOC as a precursor of a guest compound and $2 \times 10^{-3}$ mol (0.919 g) of tris(8-hydroxyquinolinate) aluminum as a host compound are dissolved in 100 ml of N,N-dimethylformamide. The homogenous solution is poured into a large excess of water, which is vigorously stirred with a homogenizer. The precipitated solid is isolated by filtration, and the residue is washed numerous with water, before drying at 80° C. in vacuo for 24 hours. Furnished is 0.773 g (yield 84%) of a green powder with green fluorescence. The powder is at-treated at 150° C.for 2.5 hours, affording a yellowish green powder with yellowish orescence. The fluorescence properties are given in table 3.

Example B2

$1 \times 10^{-5}$ mol (0.00513 g) of QA-BOC as a precursor of a guest compound and $2 \times 10^{-3}$ mol (0.919 g) of tris(8-hydroxyquinolinate) aluminum as a host compound are dissolved in 150 ml of N,N-dimethylformamide. The homogenous solution is poured into a large excess of water which is vigorously stirred with a homogenizer. The precipitated solid is isolated by filtration, and washed numerous times with water and dried at 80° C. in vacuo for 24 hours. Furnished is 0.632 g (yield 68%) of a green powder with green fluorescence. The powder is in turn heat-treated at 180° C. for 1 hour, affording a yellowish green powder with yellowish green fluorescence. The fluorescence properties are given in table 3.

TABLE 3

| Example | Host | Guest | Peak Wavelength (nm) | Peak Intensity |
|---|---|---|---|---|
| B1 | Alq3 | CIDPP | 549 | 585 |
| B2 | Alq3 | QA | 538 | 528 |

C) APPLICATION EXAMPLES

The luminance of examples C1 to C3 are measured using a luminometer (LS-110, Minolta Camera Co. Ltd.) attached with close-up lens (No.110, maximum focusing distance 205 mm, target diameter at maximum focusing distance 0.5 mm) at its maximum focusing distance.

Example C1

Electroluminescent Element (EL) with Pigment Dissolved in a Polymer Film

Fluorophore precursors used herein are DPP-BOC, MeDPP-BOC, tBuDPP-BOC, PhDPP-BOC, CIDPP-BOC, (prepared in analogy to examples 1, 4, 3, 9, and 2 of EP-A 648 770) and QA-BOC (prepared in analogy to example 1 of EP-A 648 817), which provide upon heat-treatment DPP, MeDPP, tBuDPP, PhDPP, CIDPP and QA, respectively.

Each of the fluorophore precursors as a light-emitting material, 2-(4'-tert.-butylphenyl)-5-(4"-biphenyl)-1,3,4-oxadiazole (PBD, melting point in the range of ca. 135 to 140° C., commercially available from Dojindo Laboratories) as an electron-transport material and poly(N-vinylcarbazole) (PVCz, molecular weight in the range of 400,000 to 600,000 g/mol; Kanto Chemical Co. Ltd.) as a hole-transport material, are dissolved in 1,2-dichloroethane, with a ratio of precursor:PBD:PVCz=1:20:80 (mol %), to yield a clear, homogeneous solution of the mixed components (all solutions 1.4 w/w %). The mixture is then cast onto an ITO glass substrate using a spin-coater (1H-IIID, Kyoei Semiconductor) and the solvent removed to form a light-emitting layer with a thickness of 100 nm. Next, on the light-emitting layer, magnesium as a cathode layer is deposited under a vacuum of $5.0 \times 10^{-6}$ Torr and a depositing rate of 0.01 nm/sec to a film thickness of 200 nm.

The elements obtained are heat-treated at 150° C. for 30 minutes. The parent pigment is thus in the molecularly dissolved state.

Using the ITO side as the anode and the magnesium side as the cathode, a bias of 15 V is applied to the elements and the resultant EL properties are measured using a luminometer (LS-110, Minolta Camera Co. Ltd.) and a spectro multi-channel photo detector (IMUC-7000, Ohtsuka electronics Co. Ltd.).

When the EL properties of an element doped with QA, as a fluorophore, are measured at the current of 0.86 A/cm$^2$, luminance of 300 cd/m$^2$ is observed with a peak wavelength of 540 nm.

Example C2
EL Element Prepared by Sublimation of Pigment Doped Powder.

On an ITO glass substrate, N,N'-diphenyl-N,N'-bis(3-methylphenyl)-1,1'-biphenyl-4,4'-diamine (TPD; prepared in analogy to example 1 of U.S. Pat. No. 4,265,990) is deposited, as a hole-transport substance, by vacuum deposition under a vacuum of $6.0 \times 10^{-6}$ Torr and at a depositing rate of 0.08 nm/sec to a thickness of 50 nm, to form a hole-transport layer. Next, on the hole-transport layer thus prepared, the pigment doped powder according to example B2 is deposited, as a light-emitting material, under the deposition condition of $6.0 \times 10^{-6}$ Torr, at a depositing rate of 0.08 nm/sec to a thickness of 50 nm, to form a light-emitting layer. And finally on the light-emitting layer, magnesium is deposited, as a cathode layer, to a film thickness of 200 nm.

When the EL properties of the element doped with QA, as a fluorophore, are measured at the current of 0.92 A/cm$^2$, luminance of 15500 cd/m$^2$ is observed with a peak wavelength of 540 nm.

Example C3
EL Element Prepared by Sublimation of Pigment Precursor Doped Powder.

The procedure of example C2 is repeated, however this time a precursor doped powder according to example B2 before heat-treatment, which composed of QA-BOC and Alq3, is used as a deposition source for the light-emitting layer.

When the EL properties of the element are measured at the current of 0.86 A/cm2, luminance of 12200 cd/m$^2$ is observed with a peak wavelength of 540 nm.

What is claimed is:

1. A composition comprising a polymer matrix or a polymer precursor, a host chromophore, and a pigment precursor, wherein the absorption spectrum of the pigment (as guest chromophore), obtained from the pigment precursor, overlaps with the fluorescence emission spectrum of the host chromophore.

2. Process for the creation of fluorescent radiation by exciting either electrically or by UV or visible radiation, or both, a fluorescent composition according to claim 1.

3. A composition obtained by (1) mixing a host chromophore and a fluorescing effective amount of a pigment precursor in a solvent, then generating a pigment as guest chromophore in-situ from the pigment precursor, and, subsequently, isolating the mixture of the host and guest chromophores thereby forming a solid solution, or (2) mixing a polymer as a matrix or a polymer precursor and a pigment precursor in a solvent, in the presence of a chromophore being a host component, then generating a pigment in-situ from the pigment precursor, and, subsequently, isolating the mixture of polymer and pigment, and the host component, thereby forming a solid solution, wherein the absorption spectrum of the pigment (guest chromophore) overlaps with the fluorescence emission spectrum of the host chromophore, wherein the pigment is selected from the group consisting of quinacridones, anthraquinones, perylenes, indigos, quinophthalones, isoindolinones, phthalocyanines, diketo- and dithioketopyrrolopyrroles, and azo pigments, and wherein the host chromophore is selected from the group consisting of fluorescent anthracenes, oxazoles, pyrenes, coumarines, fluoresceines, rhodamines, perylenes, perinones, isoindolones and metal complexes consisting of metals and organic ligands.

4. Process for the creation of fluorescent radiation by exciting either electrically or by UV or visible radiation, or both, a fluorescent composition according to claim 3.

* * * * *